(12) United States Patent
Weichert et al.

(10) Patent No.: US 9,345,718 B1
(45) Date of Patent: May 24, 2016

(54) PHOSPHOLIPID ETHER ANALOGS AS CANCER-TARGETING DRUG VEHICLES

(71) Applicant: Cellectar Biosciences, Inc., Madison, WI (US)

(72) Inventors: Jamey P. Weichert, Fitchburg, WI (US); Anatoly Pinchuk, Fitchburg, WI (US); Kevin Kozak, Madison, WI (US); Marc Longino, Verona, WI (US); Joseph Grudzinski, Madison, WI (US); Benjamin Titz, Madison, WI (US); Chorom Pak, Madison, WI (US); Nathan Stehle, Madison, WI (US)

(73) Assignee: CELLECTAR BIOSCIENCES, INC., Madison, WI (US)

( * ) Notice: Subject to any disclaimer, the term of this patent is extended or adjusted under 35 U.S.C. 154(b) by 0 days.

(21) Appl. No.: 14/934,209

(22) Filed: Nov. 6, 2015

Related U.S. Application Data

(60) Provisional application No. 62/080,436, filed on Nov. 17, 2014.

(51) Int. Cl.
*A61K 31/665* (2006.01)
(52) U.S. Cl.
CPC .................................... *A61K 31/665* (2013.01)
(58) Field of Classification Search
CPC .......................... A61K 31/665; A61K 51/0489
See application file for complete search history.

(56) References Cited

U.S. PATENT DOCUMENTS

| | | | |
|---|---|---|---|
| 5,534,499 A * | 7/1996 | Ansell | A61K 9/1271 424/1.21 |
| 7,632,644 B2 | 12/2009 | Weichert et al. | |
| 7,700,075 B2 | 4/2010 | Weichert et al. | |
| 7,811,548 B1 | 10/2010 | Pinchuk et al. | |
| 7,893,286 B2 | 2/2011 | Pinchuk et al. | |
| 8,535,641 B2 | 9/2013 | Weichert et al. | |
| 8,540,968 B2 | 9/2013 | Weichert et al. | |
| 8,871,181 B2 | 10/2014 | Pinchuk et al. | |
| 8,877,159 B2 | 11/2014 | Weichert et al. | |
| 8,877,160 B2 | 11/2014 | Weichert et al. | |
| 2012/0156133 A1 | 6/2012 | Pinchuk et al. | |
| 2013/0343991 A1 | 12/2013 | Weichert et al. | |
| 2015/0030538 A1 | 1/2015 | Weichert et al. | |
| 2015/0044142 A1 | 2/2015 | Pinchuk et al. | |
| 2015/0093330 A1 | 4/2015 | Weichert et al. | |

OTHER PUBLICATIONS

Bao S. et al., Stem cell-like glioma cells promote tumor angiogenesis through vascular endothelial growth factor, Cancer Res, Aug. 15, 2006, 66(16), 7843-8.
Sathornsumetee S. et al., Phase II trial of bevacizumab and erlotinib in patients with recurrent malignant glioma, Neuro Oncol, Dec. 2010, 12(12), 1300-10.
Weichert J.P., et al., Alkylphosphocholine analogs for broad-spectrum cancer imaging and therapy, Sci Transl Med, Jun. 11, 2014, 6(240), 240ra75.
Tranoy-Opalinski I, et al., Design of self-immolative linkers for tumour-activated prodrug therapy, Anticancer Agents Med Chem, Aug. 2008, 8(6), 618-37.
Tranoy-Opalinski I, et al., β-Glucuronidase-responsive prodrugs for selective cancer chemotherapy: an update, Eur J Med Chem, Mar. 3, 2014, 74:302-13, Epub Jan. 11, 2014.
Prescott, Ed., Methods in cell biology, vol. XIV, Academic Press, New York, NY, 1976, p. 33 et seq.
Sefton, M.V., Implantable pumps, Crit Rev Biomed Eng, 1987, 14(3), 201-40.
Langer, R., New methods of drug delivery, Science, Sep. 28, 1990, 249(4976), 1527-33.
Buchwald H., et al., Long-term, continuous intravenous heparin administration by an implantable infusion pump in ambulatory patients with recurrent venous thrombosis, Surgery, Oct. 1980, 88(4), 507-16.
Saudek C.D., et al., A preliminary trial of the programmable implantable medication system for insulin delivery, N Engl J Med, Aug. 31, 1989, 321(9), 574-9.
Lermer, L., et al., The synthesis of β-keto lactones via cyclization β-keto ester dianions or the cyclization of Meldrum's acid derivatives, Can J Chem, 1992, 70(5), 1427-1445.
Mabe P.J. et al., Asymmetric radical addition of TEMPO to titanium enolates, Org Lett, Jan. 17, 2014, 16(2), 516-9, Epub Dec. 31, 2013.
Cohen J.D., et al., Intracranial C6 glioma model in adult Wistar-Furth rats, J Neurooncol, Feb. 1990, 8(1), 95-6.
Weichert J.P., et al., Radioiodination via isotope exchange in pivalic acid, Int J Appl Rad Isotopes, 1986, 37(8), 907-13.
Arpicco S. et al., Preparation and characterization of novel poly(ethylene glycol) paclitaxel derivatives, Int J Pharm, Oct. 1, 2013, 454(2), 653-9, Epub May 20, 2013.
Goldmacher V.S., et al., Antibody-drug conjugates: using monoclonal antibodies for delivery of cytotoxic payloads to cancer cells, Ther Deliv, Mar. 2011, 2(3), 397-416.
Snyder F., et al., The occurrence and metabolism of alkyl and alk-1-enyl ethers of glycerol in transplantable rat and mouse tumors, Cancer Res, May 1968, 28(5), 972-978.
Snyder F., et al. Alkyl and alk-1-enyl ethers of glycerol in lipids from normal and neoplastic human tissues, Cancer Res, Jan. 1969, 29(1), 251-257.

\* cited by examiner

*Primary Examiner* — Sudhakar Katakam
(74) *Attorney, Agent, or Firm* — Wood, Phillips, Katz, Clark & Mortimer

(57) ABSTRACT

The present invention is directed to therapeutic compounds capable of targeting cancer cells and cancer stem cells. The present invention is further directed to compositions comprising these therapeutic compounds and methods of treating cancer comprising administering these therapeutic compounds.

2 Claims, 15 Drawing Sheets

MDA-MB-468

PHOSPHOLIPID ETHER ANALOGS AS CANCER-TARGETING DRUG VEHICLES

BACKGROUND OF THE INVENTION

In 2012, 14.1 million people were diagnosed with cancer worldwide and 8.2 million died of cancer. In the United States, around 40% of all people will be diagnosed with cancer during their lifetime. Despite receiving the best treatment available, 44% of those Americans will die from cancer.

Cancer is the result of a cell dividing without limitation. Healthy cells have checkpoints that prevent unlimited cell division. A few examples of these checkpoints are nutrient availability, DNA damage and contact inhibition (i.e. a cell comes into contact with another cell). Additionally, most cells can replicate only a finite number of times and thus are programmed to die after a particular number of cell divisions.

Cancer is the result of a cell overcoming these built-in checkpoints and proliferating beyond control. This uncontrolled proliferation leads to the formation of a tumor. There are two types of tumors, benign and malignant. Benign tumors are incapable of crossing natural boundaries between tissue types. Malignant tumors, on the other hand, are capable of invading nearby tissue or entering the bloodstream and metastasizing to a different location. Only malignant tumors are considered cancerous. It is this ability to infiltrate and metastasize that makes cancer such a deadly disease.

To further complicate the fight against cancer, malignant tumors have distinct cell types. One particularly troublesome type is cancer stem cells ("CSC's"). CSC's are capable of self-renewing and differentiating into the distinct types of cancer cells found in a malignant tumor. Thus, CSC's are a primary factor in the metastatic ability of a tumor. CSC's often survive radiation and chemotherapy. It is hypothesized that recurrence of cancer after radiation and chemotherapy is the result of the inability of radiation and chemotherapy to kill all CSC's combined with the ability of CSC's to establish a new tumor.

A particularly troublesome type of cancer is brain cancer. Brain cancers, such as high-grade gliomas, are often treated with surgery followed by radiation therapy. Surgery for brain tumors is often very complicated. The surgeon must remove the tumor without damaging any nearby brain tissue that could result in physical or cognitive disabilities. Often the surgeon is incapable of removing the boundaries of the tumor that contact the healthy tissue. Radiation therapy is often used to kill these remaining cancer cells. However, radiation doses are limited by the potential damage to healthy brain tissue. Unfortunately, brain cancer is usually chemotherapy resistant. This resistance is largely attributable to the blood-brain barrier ("BBB"). The BBB is a physical barrier that separates the fluid surrounding the brain from blood cells and other components in the blood stream. Most anti-cancer drugs are unable to cross the BBB.

One method of treating brain cancer is to inhibit the growth of new blood vessels that are necessary for tumor size progression. Bevacizumab marketed under the trademark Avastin® (Avastin is a registered trademark of Genentech, Inc.) is used to stop and even reverse tumor vascularization. However, Rich J., and colleagues, *Canc Res*, 2006, 66, 7843, found that when Avastin® was used to treat a glioma stem cell derived brain tumor it resulted in hypoxia and a lowered pH. Sathornsumetee S., Phase II trial of bevacizumab and erlotinib in patients with recurrent malignant glioma, *Neuro-Oncol*, 2010, December, 12(12), 1300-1310. Hypoxia and low pH are both known to cause CSC propagation and can promote CSC-driven tumor recurrence.

Chemotherapy is a term used to describe a particular type of cancer treatment that includes using cytotoxic anti-cancer drugs. Cytotoxic drugs used during chemotherapy can be broken down into several main categories including alkylating agents, antimetabolites, anti-tumor antibiotics, topoisomerase inhibitors, and mitotic inhibitors. Cytotoxic anti-cancer drugs typically cause cell division to cease and thus affect healthy tissue as well as cancerous tissue. Alkylating agents stop cancer cell division by damaging the DNA of the cancer cell. Some common alkylating agents used to treat cancer are nitrogen mustards (e.g. cyclophosphamide (Cytoxan®; Cytoxan is a registered trademark of Baxter International), nitrosoureas, alkyl sulfonates, triazeines, and ethylenimines. Platinum drugs, such as cisplatin and carboplatin, work similarly to alkylating agents. Antimetabolites stop cancer cell division by inhibiting DNA and RNA synthesis. Some common antimetabolites used to treat cancer are 6-mercaptopurine, gemcitabine (Gemzar®; Gemzar is a registered trademark of Eli Lilly and Company), methotrexate and pemetrexed (Alimta®; Alimta is a registered trademark of Eli Lilly and Company). Topoisomerase inhibitors stop cancer cell division by inhibiting topoisomerase enzymes from separating the DNA for replication. Some common topoisomerase inhibitors are topotecan, irinotecan, etoposide, and teniposide. Mitotic inhibitors stop cancer cell division by inhibiting key cell division enzymes. Some common mitotic inhibitors are taxanes (e.g. paclitaxel (Taxol®; Taxol is a registered trademark of Bristol-Myers Squibb Company) and docetaxel (Taxotere®; Taxotere is a registered trademark of Aventis Pharma SA)), epothilones, and vinca alkaloids.

One disadvantage of all of these anti-cancer drugs is the damage that they do to healthy tissue. Because the drugs treat cancer by inhibiting normal cell function, healthy tissue that also relies on constant cell division such as blood cells, mucosal surfaces and skin, can be severely damaged as well. This damage results in significant morbidity and can limit the amount of chemotherapy that can safely be delivered. Examples of side effects that occur during chemotherapy treatment include low blood count, hair loss, muscle and joint pain, nausea, vomiting, diarrhea, mouth sores, fever, and chills. To overcome this problem drugs are being developed that affect proteins and cellular functions that occur only in cancer cells. Some of these specific cancer drugs are imatinib (Gleevec®; Gleevec is a registered trademark of Novartis AG), gefitinib (Iressa®, Iressa is a registered trademark of AstraZeneca UK Limited), sunitinib (Sutent®; Sutent is a registered trademark of C.P. Pharmaceuticals, International C.V.), and bortezomib (Velcade®; Velcade is a registered trademark of Millennium Pharmaceuticals, Inc.). However, these drugs are not approved for the treatment of all cancer types and are universally associated with the development of treatment resistance. Thus, a need exists in the art for an anti-cancer drug delivery vehicle that can deliver potent, effective, broad spectrum anti-cancer drugs to cancer cells including CSC's while avoiding substantial uptake of the drug by healthy cells. Additionally, the anti-cancer drug delivery vehicle should be able to cross the BBB and deliver the anti-cancer drug to cancer cells of the brain.

Currently, there are few chemical compounds that preferentially target cancer cells. One such compound is CLR1404. Generally, CLR1404 is a promising new tumor-selective diagnostic imaging agent used to monitor the treatment response of several tumor treatment modalities. Radioiodinated CLR1404, a second-generation phospholipid ether ("PLE") analog with the following structure,

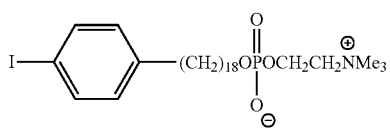

has displayed remarkable tumor selectivity in 55/60 xenograft, orthotopic and transgenic cancer and cancer stem cell derived animal models making the core molecule an ideal platform for an anti-cancer drug delivery vehicle. See U.S. Pat. No. 8,535,641; U.S. Patent Application Publication No. 2014/0030187 and Weichert, J. P., et al., Alkylphosphocholine analogs for broad-spectrum cancer imaging and therapy, *Sci Transl Med,* 2014, June 11, 6(240), 240ra75; each of which are incorporated by reference herein in its entirety.

What is not known is whether a compound that is selectively sequestered and retained by cancer cells and cancer stem cells is capable of delivering an anti-cancer drug to these same cells. Further, it is not known whether this compound is also capable of transporting anti-cancer drugs across the BBB to treat brain cancers. Finally, it is unknown whether this or similar compounds can cause the cancer cell to retain the anti-cancer drug in sufficient quantities and for a sufficient period of time to eradicate the tumor and prevent further growth and metastasis. The present invention adapts the CLR1404 core molecule for use as an anti-cancer drug delivery vehicle capable of targeting the anti-cancer drug to cancer cells and cancer stem cells including brain cancer cells. Further, the compounds of the present invention are retained in cancer cells.

SUMMARY OF THE INVENTION

The present invention is directed to therapeutic compounds capable of targeting cancer cells and cancer stem cells including brain tumor cells. The present invention is also directed to therapeutic compounds capable of being sequestered and retained by cancer cells and cancer stem cells including brain tumor cells in sufficient quantity and for sufficient duration to treat the cancer and prevent metastasis and recurrence.

In one embodiment, the present invention is directed to a therapeutic compound of the formula A-B-D wherein:

A is at least one compound of formula (I),

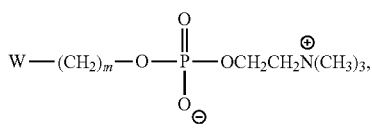

at least one compound of formula (II),

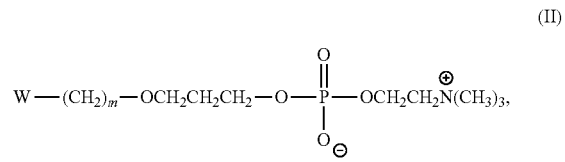

at least one compound of formula (III),

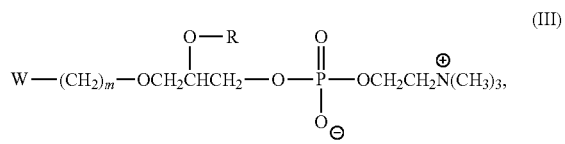

or a combination thereof, wherein W is selected from the group consisting of an aryl, a $C_1$-$C_6$ alkyl, an alkenyl, an optionally substituted $C_3$-$C_6$ cycloalkyl and an optionally substituted $C_3$-$C_6$ heterocycloalkyl, wherein R is H or an alkyl and wherein m is an integer from 12 to 24;

B is a linker compound, preferably a bond or a compound of formula (IV), Y—$(CH_2)_n$—Z (IV), wherein:
Y is bound to A;
Z is bound to D;
Y is selected from the group consisting of a bond, O, NH, C=O, NHSO$_2$O, and OC(=O)O;
Z is selected from the group consisting of O, NH, C=O, C(=O)O, C(=O)NH, SO$_2$, OC(=O)OCH$_2$, and —S—S—; and
n is an integer from 0 to 6; and
D is an anti-cancer drug, wherein the ratio of A to D is from 1:2 to 2:1.

In another embodiment, the present invention is directed to a therapeutic compound of the formula A-B-D selected from the group consisting of

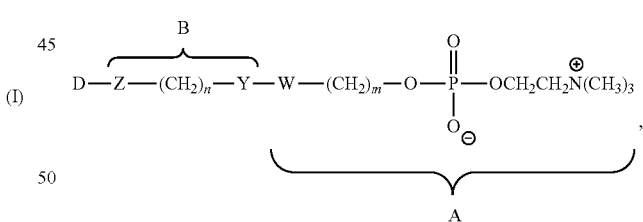

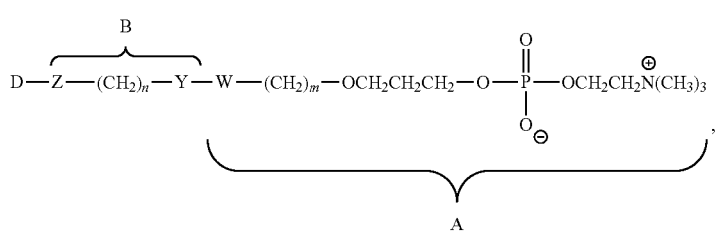

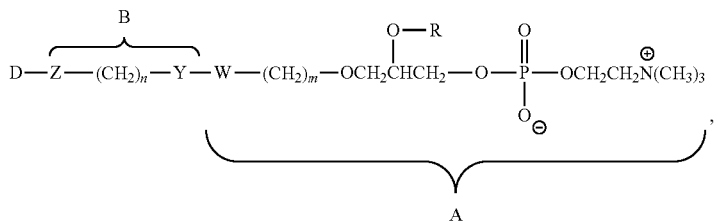

and a combination thereof, wherein:
- W is selected from the group consisting of an aryl, a $C_1$-$C_6$ alkyl, an alkenyl, an optionally substituted $C_3$-$C_6$ cycloalkyl and an optionally substituted $C_3$-$C_6$ heterocycloalkyl;
- R is H or an alkyl;
- m is an integer from 12 to 24;
- Y is selected from the group consisting of a bond, O, NH, C=O, NHSO$_2$O, and OC(=O)O;
- Z is selected from the group consisting of O, NH, C=O, C(=O)O, C(=O)NH, SO$_2$, OC(=O)OCH$_2$, and —S—S—;
- n is an integer from 0 to 6; and
- D is an anti-cancer drug, wherein B is optionally a bond between A and D.

In a preferred embodiment, the present invention is directed to a therapeutic compound of the formula A-B-D wherein:
- A is compound of formula (I), wherein W is selected from the group consisting of a $C_1$ alkyl,

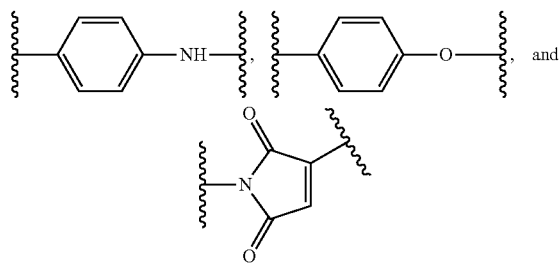

and wherein m is 18;
- B is a linker compound selected from a bond and a compound of formula (IV), Y—(CH$_2$)$_n$—Z (IV), wherein n is an integer from 0 to 6, Y is bound to A, Z is bound to D, Y is selected from the group consisting of a bond and C=O and Z is selected from the group consisting of NH, C=O, C(=O)NH and C(=O)O; and
- D is selected from the group consisting of paclitaxel, irinotecan, topotecan, gemcitabine, cisplatin, geldanamycin and mertansine.

In a more preferred embodiment, the present invention is directed to a therapeutic compound of the formula A-B-D wherein:
- A is a compound of formula (I), wherein W is

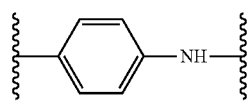

and m is 18;
- B is a compound of formula (IV), wherein Y is C=O and Z is C=O, C(=O)NH or C(=O)O and n is 3 or 4; and
- D is paclitaxel, wherein the ratio of A to D is 1:1.

In another more preferred embodiment, the present invention is directed to a therapeutic compound of the formula A-B-D wherein:
- A is a compound of formula (I), wherein W is

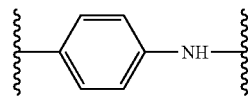 [SMILES: *Nc1ccc(*)cc1]

and m is 18;
- B is a bond or a compound of formula (IV), wherein Y is C=O, Z is NH and n is 1 or 3; and
- D is geldanamycin, wherein the ratio of A to D is 1:1.

In another more preferred embodiment, the present invention is directed to a therapeutic compound of the formula A-B-D wherein:
- A is a compound of formula (I), wherein W is

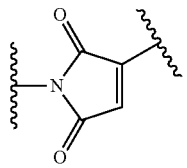 [SMILES: *C1=CC(=O)N(*)C1=O]

and m is 18;
- B is a bond; and
- D is mertansine, wherein the ratio of A to D is 1:1.

In another aspect, the present invention provides a pharmaceutical composition containing a compound of the present invention in combination with one or more pharmaceutically acceptable carriers.

In another aspect, the present invention provides a method of treating cancer comprising administering an effective amount of a therapeutic compound of the present invention to a subject with cancer.

In one embodiment, the present invention provides a method of treating cancer comprising administering an effective amount of a therapeutic compound of the present invention to a subject with cancer wherein the cancer comprises cancer stem cells.

In another embodiment, the present invention provides a method of treating cancer comprising administering an effective amount of a therapeutic compound of the present invention to a subject with cancer wherein the cancer is recurrent.

DETAILED DESCRIPTION OF THE INVENTION

Definitions

Figure 1:
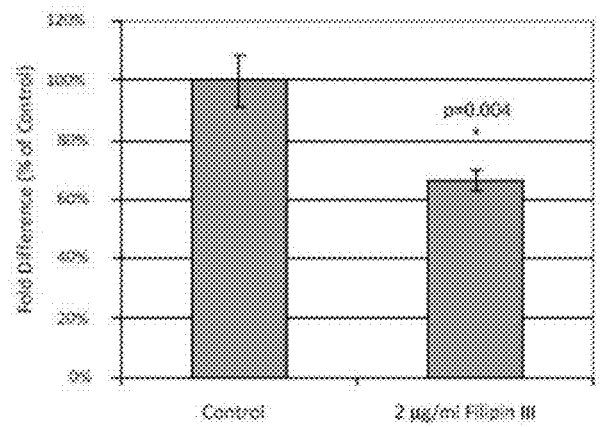
FIG. 1. Phospholipid ether ("PLE") analogs are sequestered via lipid rafts.

As used herein, the term "treating" includes preventative as well as disorder remittent treatment including reducing, suppressing and inhibiting cancer progression or recurrence. As used herein, the terms "reducing", "suppressing" and "inhibiting" have their commonly understood meaning of lessening or decreasing. As used herein, the term "progression" means increasing in scope or severity, advancing, growing or becoming worse. As used herein, the terms "recurrence" and "recurrent" refer to the return of a disease after a remission.

As used herein, the term "administering" refers to bringing a patient, tissue, organ or cells in contact with an anti-cancer compound of the present invention. As used herein, administration can be accomplished in vitro (i.e. in a test tube) or in vivo, (i.e. in cells or tissues of living organisms, for example, humans). In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-cancer substance using a PLE compound or (2) is susceptible to a disorder that is preventable by administering the anti-cancer compound of the present invention.

As used herein, the term "effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, an "effective amount" will depend upon the context in which it is being administered. An effective amount may be administered in one or more prophylactic or therapeutic administrations.

As used herein the term "therapeutic compound" refers to any chemical compound capable of providing treatment for cancer.

As used herein the term "cancer" refers to any disease that results from the uncontrolled division of cells capable of metastasizing.

The terms "chemotherapy drug" "anti-cancer drug" and "anti-tumor drug" are used interchangeably throughout the specification.

The term "malignant tumor cell" and "cancer cell" are used interchangeably throughout the specification. The term "malignant tumor stem cell" and "cancer stem cell" are used interchangeably throughout the specification.

As used herein, the term "composition" is intended to encompass a product comprising the specified ingredients in the specified amounts, as well as any product which results, directly or indirectly, from a combination of the specified ingredients in the specified amounts.

As used herein the term "A" refers to an phospholipid ether of the formula

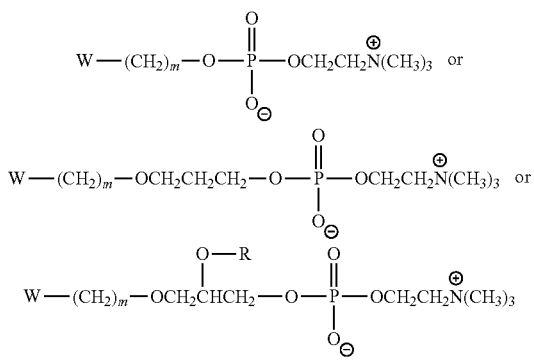

As used herein the term "W" refers to an aryl, a $C_1$-$C_6$ alkyl, an alkenyl, an optionally substituted $C_3$-$C_6$ cycloalkyl and an optionally substituted $C_3$-$C_6$ heterocycloalkyl.

As used herein the term "aryl" refers to an aromatic ring including a phenyl group.

As used herein the term "alkyl" refers to a branched or straight-chain alkyl consisting of a saturated hydrocarbon group of 1 to 24 carbon atoms ($C_1$-$C_{24}$) unless otherwise stated. The alkyl group can be cyclic or acyclic.

As used herein the term "alkenyl" refers to a carbon-carbon double bond.

As used herein the term "cycloalkyl" refers to a cyclic alkyl group of 3 to 24 carbon atoms ($C_3$-$C_{24}$).

As used herein the term "heterocycloalkyl" refers to a cyclic group of 3 to 24 atoms ($C_3$-$C_{24}$) selected from carbon, nitrogen, sulfur, phosphate and oxygen wherein at least one atom is carbon.

In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

As used herein the term "R" refers to a hydrogen (H) or an alkyl.

As used herein the term "m" refers to an integer of 12 to 24.

As used herein the term "n" refers to an integer of 0 to 6.

As used herein the term "B" refers to a linker compound. As used herein the term "linker compound" refers to any chemical compound or compounds capable of forming a chemical bond with two or more other distinct chemical compounds such that all compounds form a single larger compound. In one embodiment, the linker compound is a bond. Multiple linker compounds may be used in the formation of the larger compound. In specific embodiments, the term linker compound is a bond or a compound of the formula Y—$(CH_2)_n$—Z.

As used herein the term "Y" refers to a bond, O, NH, C=O, $NHSO_2O$, or OC(=O)O.

As used herein the term "Z" refers to O, NH, C=O, C(=O)O, C(=O)NH, $SO_2$, OC(=O)$OCH_2$, and —S—S—.

As used herein the term "D" refers to any anti-cancer drug currently known or in development.

As defined herein, the term "isomer" includes, but is not limited to optical isomers and analogs, structural isomers and analogs, conformational isomers and analogs, and the like. In one embodiment, this invention encompasses the use of different optical isomers of the present invention. It will be appreciated by those skilled in the art that the anti-cancer compounds useful in the present invention may contain at least one steriogenic center. Accordingly, the compounds used in the methods of the present invention may exist in, and be isolated in, optically-active or racemic forms. Some compounds may also exhibit polymorphism.

It is to be understood that the present invention may encompass the use of any racemic, optically-active, polymorphic, or stereroisomeric form, or mixtures thereof, which form possesses properties useful in the treatment of cancer-related conditions described and claimed herein. In one embodiment, the anti-cancer compounds may include pure (R)-isomers. In another embodiment, the anti-tumor compounds may include pure (S)-isomers. In another embodiment, the compounds may include a mixture of the (R) and the (S) isomers. In another embodiment, the compounds may include a racemic mixture comprising both (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also he prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes derivatives of the anti-cancer compounds. The term "derivatives" includes but is not limited to ether derivatives, acid derivatives, amide derivatives, ester derivatives and the like. In addition, this invention further includes methods utilizing hydrates of the anti-tumor compounds. The term "hydrate" includes but is not limited to hemihydrate, monohydrate, dihydrate, trihydrate and the like.

This invention further includes metabolites of the anti-cancer compounds. The term "metabolite" means any substance produced from another substance by metabolism or a metabolic process.

Cancers that can be treated with compounds of the present invention include, but are not limited to: breast cancer including male breast cancer; digestive/gastrointestinal cancers including anal cancer, appendix cancer, extrahepatic bile duct cancer, gastrointestinal carcinoid tumor, colon cancer, esophageal cancer, gallbladder cancer, gastric cancer, gastrointestinal stromal tumors ("gist"), Islet cell tumors, adult primary liver cancer, childhood liver cancer, pancreatic cancer, rectal cancer, small intestine cancer, and stomach (gastric) cancer;

endocrine and neuroendocrine cancers including pancreatic adenocarcinoma, adrenocortical carcinoma, pancreatic neuroendocrine tumors, Merkel cell carcinoma, non-small cell lung neuroendocrine tumor, small cell lung neuroendocrine tumor, parathyroid cancer, pheochromocytoma, pituitary tumor and thyroid cancer; eye cancers including intraocular melanoma and retinoblastoma; genitourinary cancer including bladder cancer, kidney (renal cell) cancer, penile cancer, prostate cancer, transitional cell renal pelvis and ureter cancer, testicular cancer, urethral cancer and Wilms tumor; germ cell cancers including childhood central nervous system cancer, childhood extracranial germ cell tumor, extragonadal germ cell tumor, ovarian germ cell tumor and testicular cancer; gynecologic cancers including cervical cancer, endometrial cancer, gestational trophoblastic tumor, ovarian epithelial cancer, ovarian germ cell tumor, uterine sarcoma, vaginal cancer and vulvar cancer; head and neck cancers including hypopharyngeal cancer, laryngeal cancer, lip and oral cavity cancer, metastatic squamous neck cancer with occult primary, mouth cancer, nasopharyngeal cancer, oropharyngeal cancer, paranasal sinus and nasal cavity cancer, parathyroid cancer, pharyngeal cancer, salivary gland cancer and throat cancer; leukemias including adult acute lymphoblastic leukemia, childhood acute lymphoblastic leukemia, adult acute myeloid leukemia, childhood acute myeloid leukemia, chronic lymphocytic leukemia, chronic myelogenous leukemia and hairy cell leukemia; lymphomas including AIDS-related lymphoma, cutaneous t-cell lymphoma, adult Hodgkin lymphoma, childhood Hodgkin lymphoma, Hodgkin lymphoma during pregnancy, mycosis fungoides, adult non-Hodgkin lymphoma, childhood non-Hodgkin lymphoma, non-Hodgkin lymphoma during pregnancy, primary central nervous system lymphoma, Sézary syndrome and Waldenström macroglobulinemia; musculoskeletal cancers including Ewing sarcoma, osteosarcoma and malignant fibrous histocytoma of bone, childhood rhabdomyosarcoma and soft-tissue sarcoma; neurological cancers including adult brain tumor, childhood brain tumor, astrocytomas, brain stem glioma, central nervous system atypical teratoid/rhabdoid tumor, central nervous system embryonal tumors, craniopharyngioma, ependymoma, neuroblastoma, primary central nervous system (CNS) lymphoma; respiratory/thoracic cancers including non-small cell lung cancer, small cell lung cancer, malignant mesothelioma, thymoma and thymic carcinoma; and skin cancers including Kaposi sarcoma, melanoma and squamous cell carcinoma.

Compounds of formula (I) of the present invention have been demonstrated to be sequestered by cancer stem cells. See, Weichert J. P., et al. (2014) at 2, FIG. 2 (demonstrating that CLR-1501, a CLR1404 fluorescent analog, has enhanced uptake by human glioblastoma stemlike cells and serum-cultured human glioblastoma cells as compared to normal human astrocytes and fetal human neural stem cells.) Cancer stem cells are associated with most, if not all, major cancer types. Tumor hypoxia stimulates cancer stem cell propagation, leading to increased resistance and metastatic potential. As such, cancer stem cells are associated with chemotherapy resistance, tumor re-growth, and metastasis following chemotherapy and radiation therapy. Thus, compounds of the present invention have the potential to treat various forms of cancer that have proven resistant to traditional therapy regimens.

Compounds of the Invention

Drug delivery vehicles that are useful for the present invention include, but are not limited to, compounds of formula (I),

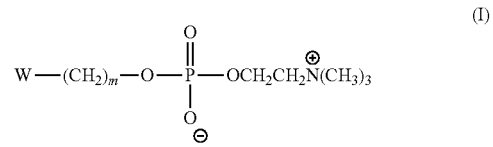

or formula (II),

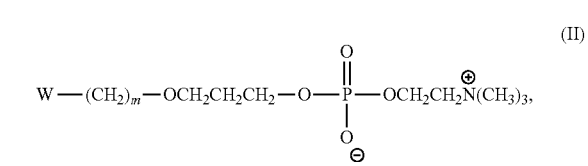

or formula (III)

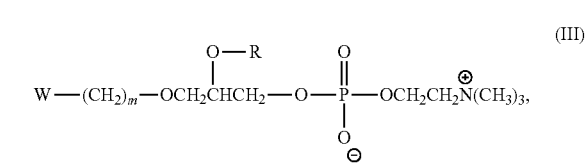

or a combination thereof, wherein W is selected from the group consisting of an aryl, a $C_1$-$C_6$ alkyl, an alkenyl, an optionally substituted $C_3$-$C_6$ cycloalkyl and an optionally substituted $C_3$-$C_6$ heterocycloalkyl, wherein R is H or an alkyl and wherein m is an integer from 12 to 24.

The basis for selective tumor targeting of compounds of the present invention lies in differences between the plasma membranes of cancer cells as compared to those of most normal cells. Specifically, cancer cell membranes are highly enriched in "lipid rafts". Cancer cells have five to ten times more lipid rafts than healthy cells. Lipid rafts are specialized regions of the membrane phospholipid bilayer that contain high concentrations of cholesterol and sphingolipids and serve to organize cell surface and intracellular signaling molecules (e.g., growth factor and cytokine receptors, the phosphatidylinositol 3-kinase (PI3K)/Akt survival pathway). Data suggests that lipid rafts serve as portals of entry for PLEs. The marked selectivity of these compounds for cancer cells versus non-cancer cells is attributed to the high affinity of PLEs for cholesterol and the abundance of cholesterol-rich lipid rafts in cancer cells. The pivotal role played by lipid rafts is underscored by the fact that disruption of lipid raft architecture suppresses uptake of PLEs into cancer cells. It has been shown that the uptake of PLE's is reduced by 60% when lipid rafts are blocked from forming. (See Example 2 and FIG. 1).

Preliminary results obtained in over 55 xenograft and spontaneous tumor models have universally shown CLR1404 to undergo selective uptake and prolonged retention in tumors. Because the agent is metabolized to some extent in the liver, the inventors avoided earlier compound evaluation in liver tumor models due to high liver background radioactivity levels.

Figure 3:
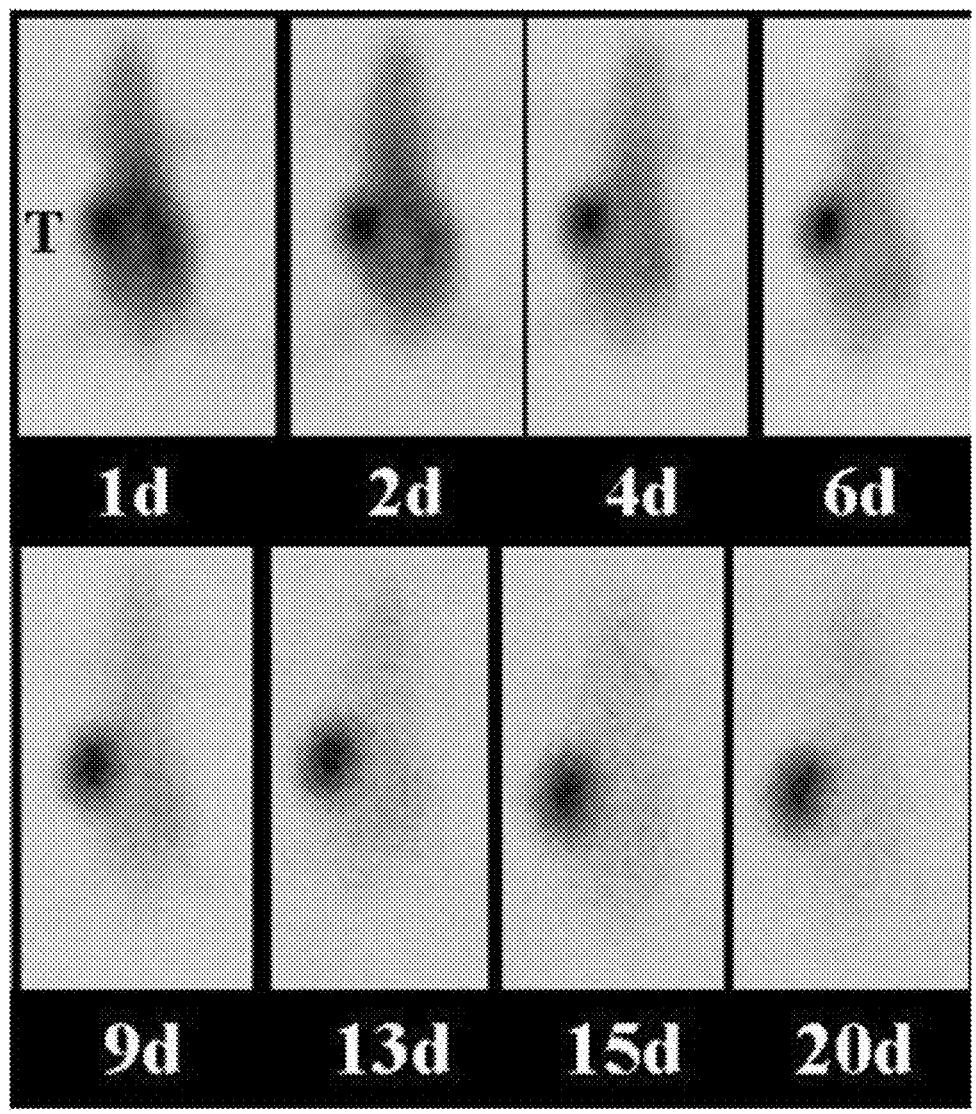
FIG. 3. Prolonged retention of $^{131}$I-CLR1404 by human RL-251 tumor xenograft in SCID mouse.

CLR1404 is a PLE. Results obtained in a variety of tumor models indicate that CLR1404 is sequestered and selectively retained by cancer cells and cancer stem cells. In fact, CLR1404 has been shown to remain in cancer cells for up to 20 days. See FIG. 3. CLR1404 localizes in both primary and metastatic lesions regardless of anatomic location including those found in lymph nodes. See Examples 3-8. The high tumor to background avidity and tumor selectivity of CLR1404 suggests the core molecule is well-suited for use as an anti-cancer drug delivery vehicle.

Linker compounds that are useful for the present invention include any chemical linker capable of binding a drug delivery vehicle of the present invention to an anti-cancer drug of the present invention. Linker compounds that are useful for the present invention include both cleavable and non-cleavable linkers. In one embodiment, linker compounds that are useful for the present invention include, but are not limited to, aminobutyramide, amino acids, glutaramic acids, dicarboxylic acids, carbamic acids, a carbonyl, 9,10-anthracenedicarboxylic acid, biphenyl-3,3',5,5'-tetracarboxylic acid, biphenyl-3,4',5-tricarboxylic acid, 5-bromoisophthalic acid, 5-cyano-1,3-benzenedicarboxylic acid, 2,2'-diamino-4,4'-stilbenedicarboxylic acid, 2,5-diaminoterephthalic acid, 2,5-dihydroxyterephthalic acid, 5-ethynyl-1,3-benzenedicarboxylic acid, 2-hydroxyterephthalic acid, imidazole, 2-methylimidazole, 2,6-naphthalenedicarboxylic acid, oxalic acid dehydrate, terephthalic acid, [1,1':4',1"]terphenyl-3,3",5,5"-tetracarboxylic acid, 3,3',5,5'-tetracarboxydiphenylmethane, 1,2,4,5-tetrakis(4-carboxyphenyl)benzene, 4,4',4"-s-triazine-2,4,6-triyl-tribenzoic acid, trimesic acid, 1,3,5-tris(4'-carboxy[1,1'-biphenyl]-4-yl)benzene, 1,3,5-tris(4-carboxyphenyl)benzene, and 1,3,5-triscarboxyphenylethynylbenzene.

In another embodiment, linker compounds useful for the present invention also include, but are not limited to, lysosomal protease sensitive linkers with or without an aniline-based self-immolative fragment. Non-limiting examples of lysosomal protease sensitive linkers are

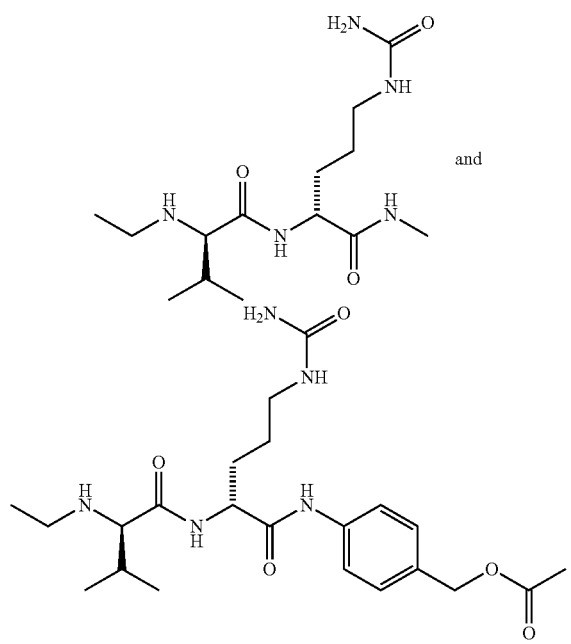

which contain the valine-citrulline dipeptide linker designed to display an optimal balance between plasma stability and intracellular protease cleavage. See, Tranoy-Opalinski I., Design of self-immolative linkers for tumour-activated prodrug therapy, *Anticancer Agents Med Chem,* 2008 August, 8(6):618-637, which is incorporated by reference herein in its entirety.

In another embodiment, linker compounds useful for the present invention also include, but are not limited to, self-immolative linkers that are cleaved by β-glucuronidase. β-glucuronidase is present in high concentration in necrotic area surrounding cancer cells. See; Tranoy-Opalinski I., β-glucuronidase-responsive prodrugs for selective cancer chemotherapy: An update, *Eur J Med Chem,* 2014 March 3, 74, 302-313, which is incorporated by reference herein in its entirety. Non-limiting examples of β-glucuronidase-cleavable self-immolative linkers are

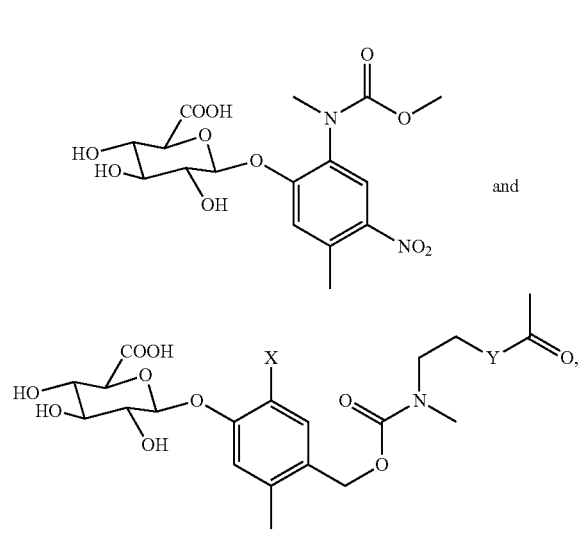

wherein X is $NH_2$ or $NO_2$ and wherein Y is O or $NCH_3$.

Preferred linker compounds of the present invention are a bond or a compound of formula (IV), Y—$(CH_2)_n$—Z (IV), wherein:

Y is bound to A;

Z is bound to D;

Y is selected from the group consisting of a bond, O, NH, C=O, $NHSO_2O$, and OC(=O)O; and Z is selected from the group consisting of O, NH, C=O, C(=O)O, C(=O)NH, $SO_2$, OC(=O)$OCH_2$, and —S—S—; and n is an integer from 0 to 6.

More preferred linker compounds of the present invention are a bond or a compound of formula (IV), wherein n is an integer from 0 to 6, Y is bound to A, Z is bound to D, Y is selected from the group consisting of a bond and C=O and Z is selected from the group consisting of NH, C=O, C(=O)NH and C(=O)O.

Anti-cancer drugs that are useful for the present invention include, but are not limited to, paclitaxel, irinotecan, topotecan, gemcitabine, cisplatin, geldanamycin, mertansine, abiraterone, afatinib, aminolevulinic acid, aprepitant, axitinib, azacitidine, belinostat, bendamustine, bexarotene, bleomycin, bortezomib, bosutinib, busulfan, cabazitaxel, cabozantinib, capecitabine, carboplatin, carfilzomib, carmustine, ceritinib, cetuximab, chlorambucil, clofarabine, crizotinib, cyclophosphamide, cytarabine, dabrafenib, dacarbazine, dactinomycin, dasatinib, daunorubicin, decitabine, denosumab, dexrazoxane, docetaxel, dolastatins (e.g. monomethyl auristatin E), doxorubicin, enzalutamide, epirubicin, eribulin mesylate, erlotinib, etoposide, everolimus, floxuridine, fludarabine phosphate, fluorouracil, ganetespib, gefitinib, gemtuzumab ozogamicin, hexamethylmelamine, hydroxyurea, ibritumomab tiuxetan, ibrutinib, idelalisib, ifosfamide, imatinib, ipilimumab, ixabepilone, lapatinib, leucovorin calcium, lomustine, maytansinoids, mechlorethamine, melphalan, mercaptopurine, mesna, methotrexate, mitomycin C, mitotane, mitoxantrone, nelarabine, nelfinavir, nilotinib, obinutuzumab, ofatumumab, omacetaxine mepesuccinate, oxaliplatin, panitumumab, pazopanib, pegaspargase, pembrolizumab, pemetrexed, pentostatin, pertuzumab, plicanycin, pomalidomide, ponatinib hydrochloride, pralatrexate, procarbazine, radium 223 dichloride, ramucirumab, regorafenib, retaspimycin, ruxolitinib, semustine, siltuximab, sorafenib, streptozocin, sunitinib malate, tanespimycin, temozolomide, temsirolimus, teniposide, thalidomide, thioguanine, thiotepa, toremifene, trametinib, trastuzumab, vandetanib, vemurafenib, vinblastine, vincristine, vinorelbine, vismodegib, vorinostat, and ziv-aflibercept. Any compounds that are currently known to or are capable of acting as anti-cancer drugs are also useful for the present invention.

PLE drug delivery vehicles of the present invention may attach singularly or in multiple to an anti-cancer drug in any number of possible stable attachment sites via a linker compound or directly.

Compositions of the Invention

In another aspect, the present invention provides a pharmaceutical composition containing a compound of the present invention in combination with one or more pharmaceutically acceptable carriers. In a preferred aspect the pharmaceutical composition is free of Kolliphor® EL (Kolliphor is a registered trademark of BASF SE). Kolliphor® EL is formerly known as Cremophor® EL (Cremophor is a registered trademark of BASF SE).

Actual dosage levels of active ingredients in the therapeutic compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more pharmaceutically acceptable carriers. The pharmaceutical compositions can be specially formulated for oral administration in solid or liquid form, for parenteral administration or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The terms "parenteral" or "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art. See, for example, Prescott, Ed., *Methods in Cell Biology*, Volume XIV, Academic Press, New York, N.Y. (1976), p. 33 et seq. Such compositions will influence the physical state, solubility, stability, rate of in vivo release, and rate of in vivo clearance.

In one method of the present invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, for example liver, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In another aspect, the invention is directed to a method of treating a disease or condition in a subject comprising administering to the subject an effective amount of a compound of the present invention.

In general, the invention is not limited to treatment of any specific disease or condition but encompasses the treatment of any disease or condition whose mechanism may be affected by the compounds of the present invention.

Representative Embodiments

Paclitaxel-CLR1404 Conjugates

In one embodiment of the present invention the therapeutic compound is paclitaxel linked to an CLR1404 core compound by a dicarboxylic acid linker, wherein the dicarboxylic acid linker is attached to the CLR1404 core compound via an amide bond and to paclitaxel via an ester bond at the 2'-OH group,

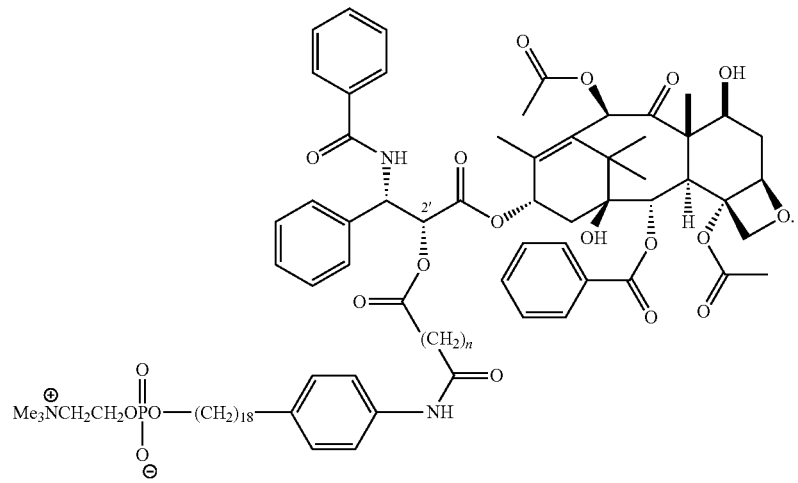

In a preferred embodiment of the present invention the therapeutic compound is paclitaxel linked to the CLR1404 core compound by a glutaramic acid linker, wherein the glutaramic acid linker is attached to the CLR1404 core compound via an amide bond and to paclitaxel via an ester bound at the 2'-OH group,

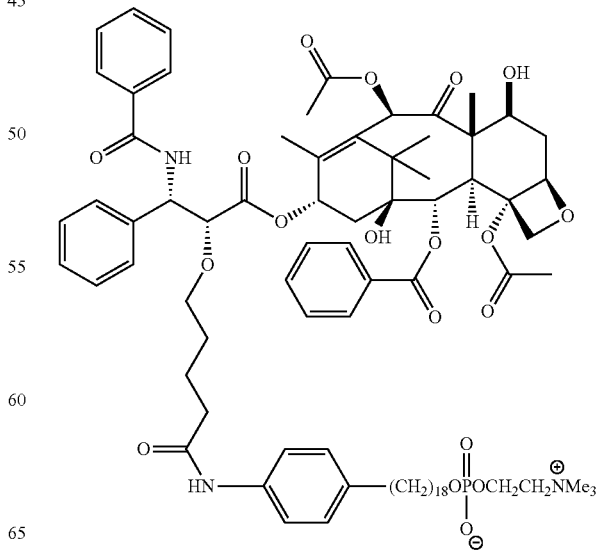

CLR1601 conjugate.

In another embodiment of the present invention the therapeutic compound is paclitaxel linked to the CLR1404 core compound by a dicarboxylic acid linker, wherein the dicarboxylic acid linker is attached to the CLR1404 core compound via an amide bond and to paclitaxel via an ester bond at the 7-OH group, In another embodiment of the present invention the therapeutic compound is paclitaxel linked to the CLR1404 core compound by a carbamic acid linker, wherein the carbamic acid linker is attached to the CLR1404 core compound via an amide bond and to paclitaxel via an ester bond at the 7-OH group,

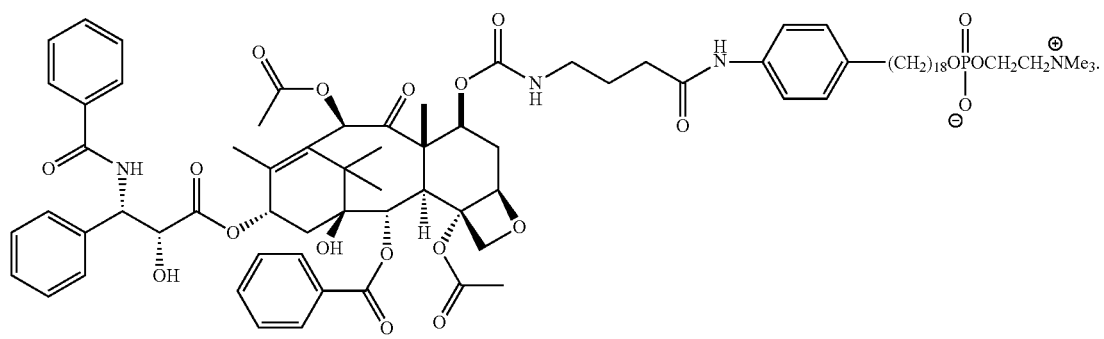

CLR1602 conjugate.

In another embodiment of the present invention the therapeutic compound is paclitaxel linked to the CLR1404 core compound by a carbonic-carboxylic acid linker, wherein the carbonic-carboxylic acid linker is attached to the CLR1404 core compound via an amide bond and to paclitaxel via an ester bond at the 7-OH group,

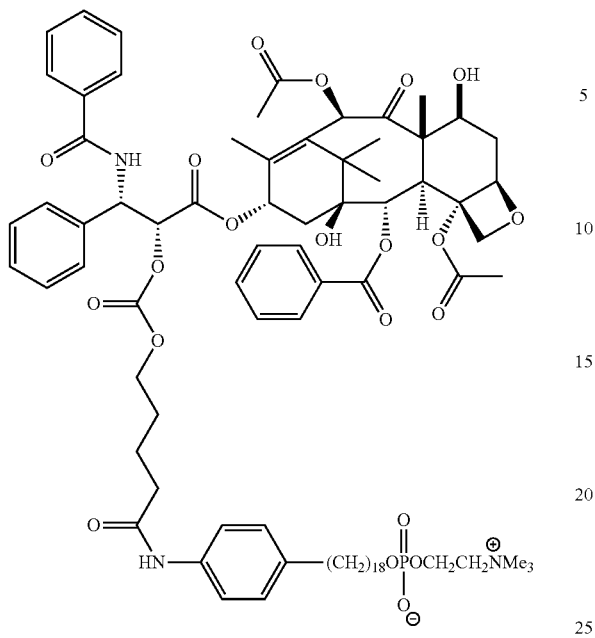

CLR1603 conjugate.

In another embodiment of the present invention the therapeutic compound is paclitaxel linked to two CLR1404 core compounds by dicarboxylic acid linkers, wherein the dicarboxylic acid linkers are attached to the CLR1404 core compounds via amide bonds and to paclitaxel via ester bonds at both the 2'-OH group and the 7-OH group,

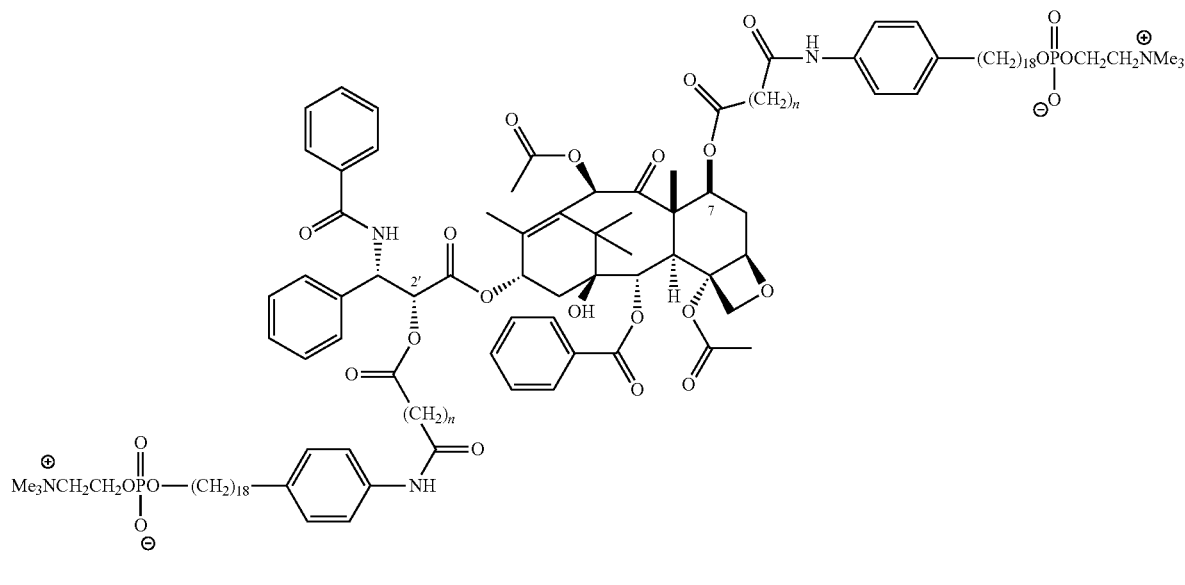

In another embodiment of the present invention the therapeutic compound is paclitaxel linked to the CLR1404 core compound by a dicarboxylic acid linker, wherein the dicarboxylic acid linker is attached to the CLR1404 core compound via an amide bond and to paclitaxel via a carbonate or a carbamate bond at the 2'-OH group,

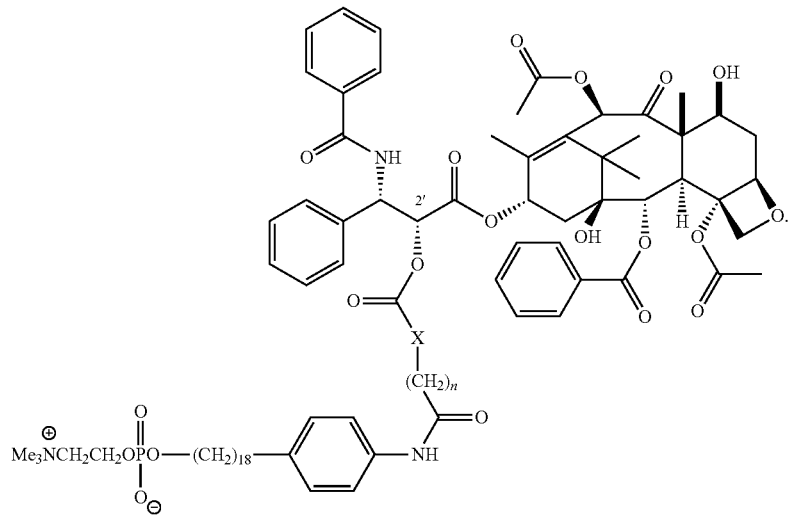

In another embodiment of the present invention the therapeutic compound is paclitaxel linked to an CLR1404 core compound by a dicarboxylic acid linker, wherein the dicarboxylic acid linker is attached to the CLR1404 core compound via an amide bond and to paclitaxel via a carbonate or a carbamate bond at the 7-OH group,

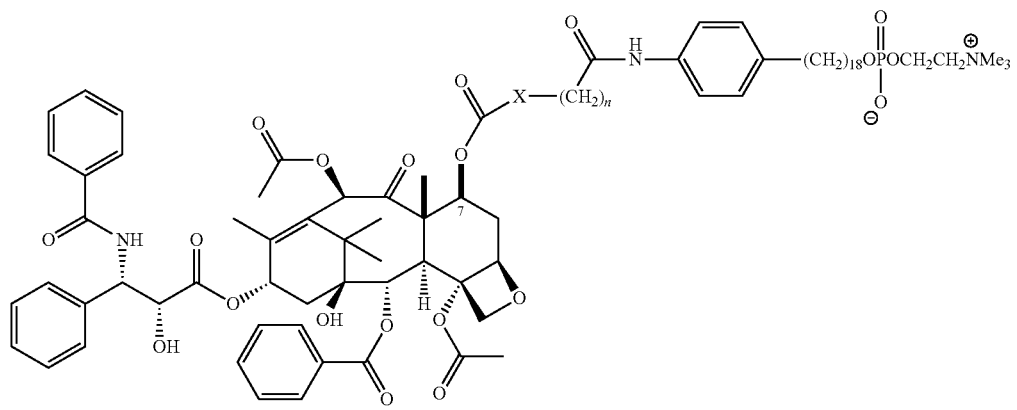

In another embodiment of the present invention the therapeutic compound is paclitaxel linked to two CLR1404 core compounds by dicarboxylic acid linkers, wherein the dicarboxylic acid linkers are attached to the two CLR1404 core molecules via amide bonds and to paclitaxel via a carbonate or a carbamate bond at both the 2'-OH group and the 7-OH group,

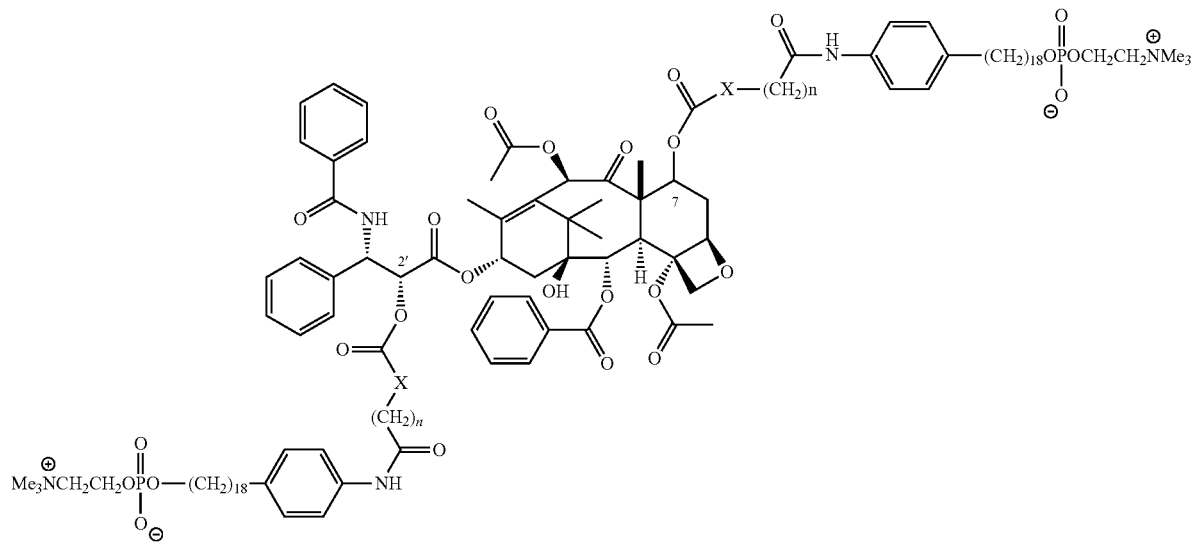

In one embodiment of the present invention the therapeutic compound is paclitaxel linked to a C18 alkyl phosphocholine compound via a carboxylic linker, wherein the carboxylic linker is attached to the C18 alkyl phosphocholine compound via an amide or carbonate bond and to paclitaxel via a carbonate or a carbamate bond at the 2'-OH group

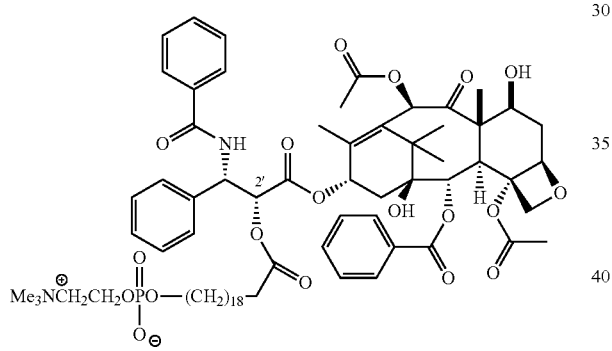

Irinotecan-CLR1404 Conjugate

In one embodiment of the present invention the therapeutic compound is irinotecan linked to the CLR1404 compound by a dicarboxylic acid linker, wherein the dicarboxylic acid linker is attached to the CLR1404 core compound via an a carbonate or a carbamate bond and to irinotecan via an ester bond,

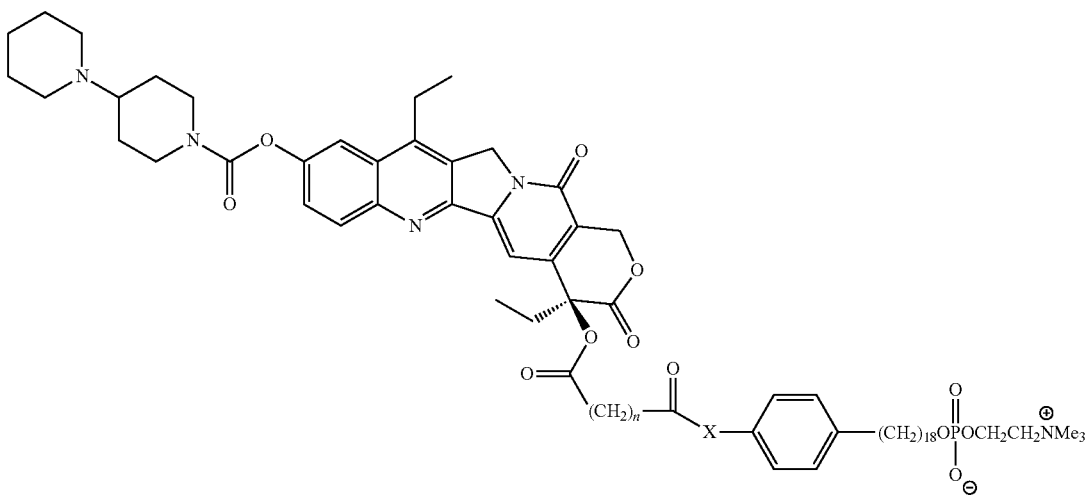

Irinotecan-C18 Alkyl Phosphocholine Conjugate

In one embodiment of the present invention the therapeutic compound is irinotecan linked to a C18 alkyl phosphocholine compound by a carbonyl linker, wherein the carbonyl linker is attached to the C18 alkyl phosphocholine compound via a carbon-carbon bond and to irinotecan via an ester bond,

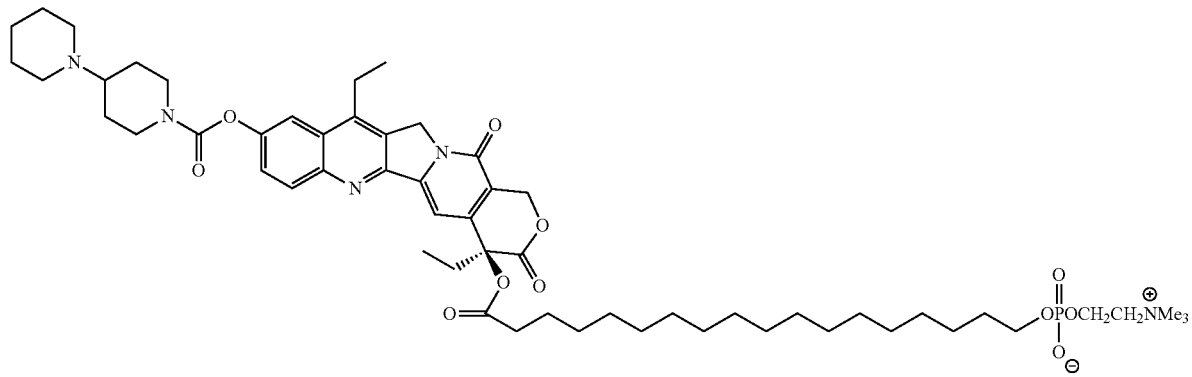

Topotecan-CLR1404 Conjugates

In one embodiment of the present invention the therapeutic compound is topotecan linked to the CLR1404 core compound by a non-hydrolyzable phenyl ether,

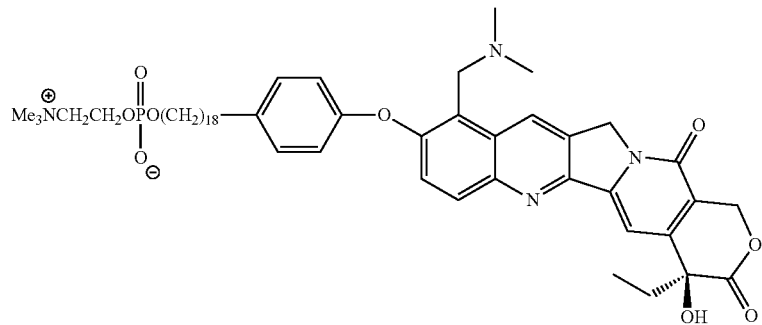

In another embodiment of the present invention the therapeutic compound is topotecan linked to an CLR1404 core compound by a dicarboxylic acid linker, wherein the dicarboxylic acid linker is attached to the CLR1404 compound via a carbonate or a carbamate bond and to topotecan via an ester bond,

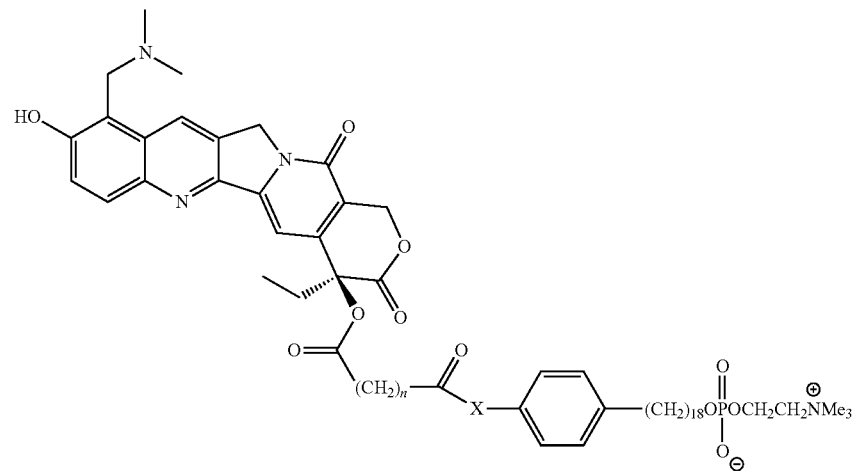

Gemcitabine-C18 Alkyl Phosphocholine Conjugate

In one embodiment of the present invention the therapeutic compound is gemcitabine linked to two C18 alkyl phosphocholine compounds by carbonyl linkers, wherein the carbonyl linkers are attached to the C18 alkyl phosphocholine compounds via carbon-carbon bonds and to gemcitabine via ester bonds,

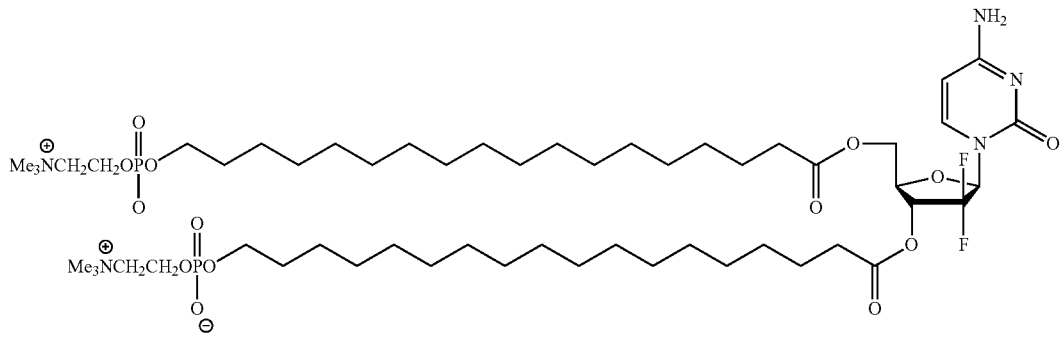

In another embodiment of the present invention the therapeutic compound is gemcitabine linked to a C18 alkyl phosphocholine compound by a carbonyl linker, wherein the carbonyl linker is attached to the C18 alkyl phosphocholine compound via a carbon-carbon bond and to gemcitabine via an ester bond,

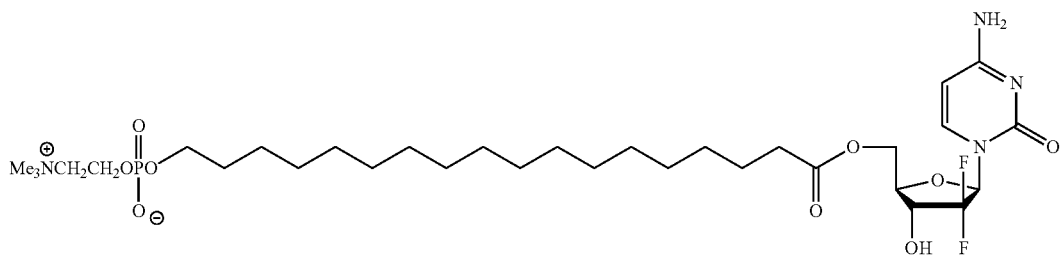

Cisplatin-CLR1404 Core Conjugate

In one embodiment of the present invention the therapeutic compound is cisplatin linked directly to the CLR1404 core compound,

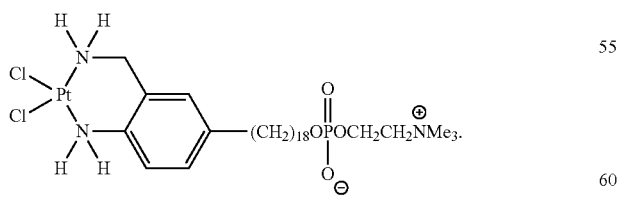

Geldanamycin-CLR1404 Conjugates

In one embodiment of the present invention the therapeutic compound is geldanamycin linked directly to the CLR1404 core compound,

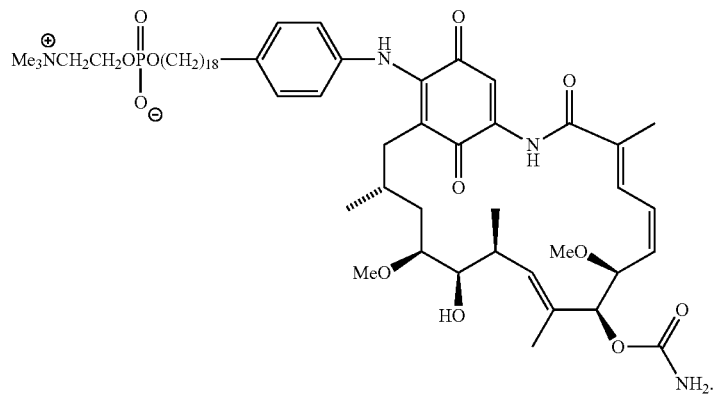

In another embodiment of the present invention the therapeutic compound is geldanamycin linked to the CLR1404 core compound by a short amino acid linker, wherein the amino acid linker is connected to the CLR1404 core compound via a carbonate or carbamate bond and to the geldanamycin via an amide bond,

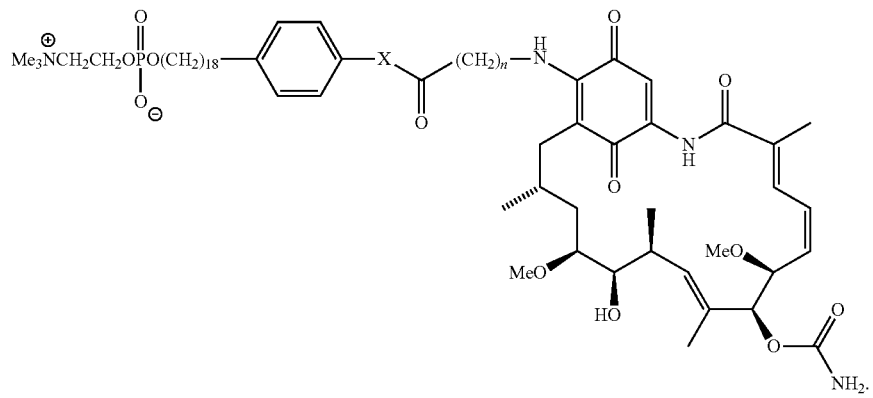

In a preferred embodiment of the present invention the therapeutic compound is geldanamycin linked to the CLR1404 core compound by an aminobutyramide linker, wherein the aminobutyramide linker is connected to the CLR1404 core compound via a carbamate bond and to the geldanamycin via an amide bond:

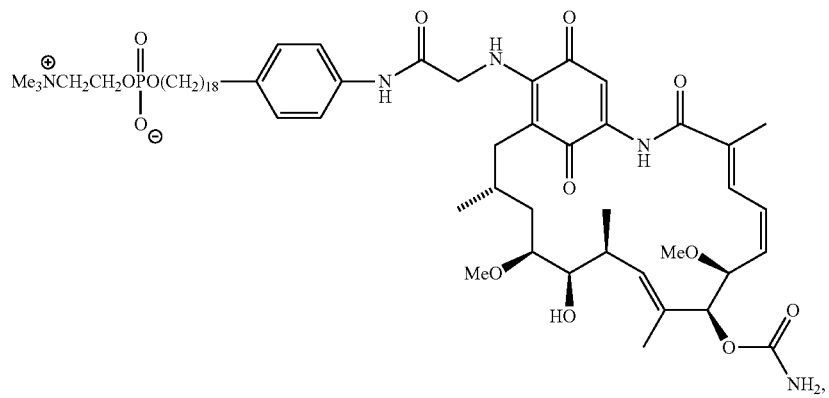

CLR1606 conjugate and

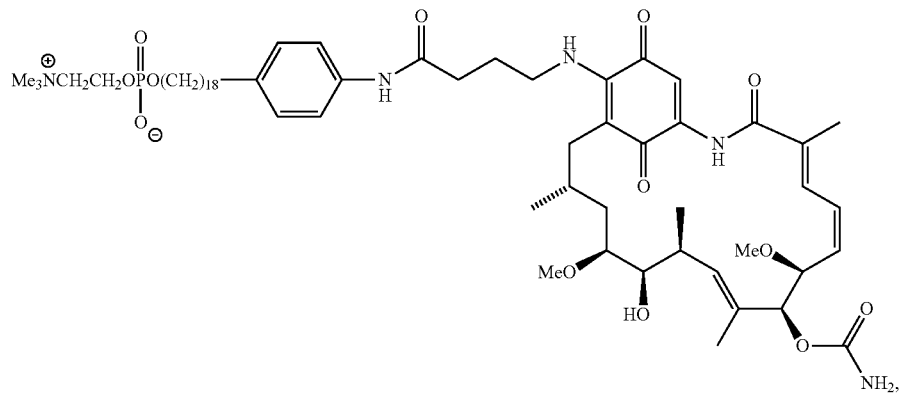

CLR1607 conjugate.

Mertansine-CLR1404 Conjugates

In another embodiment of the present invention the therapeutic compound is mertansine linked to the CLR1404 core compound by a maleimide linker, wherein the maleimide linker is attached to the CLR1404 core compound via an amide bond and to mertansine via a carbon-sulfur bond,

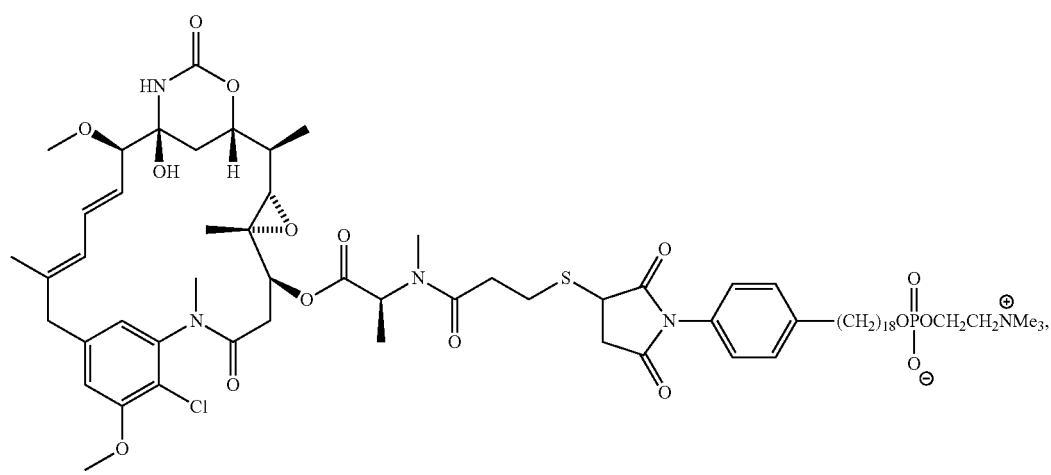

CLR1608 conjugate.

For all representative embodiments n is an integer from 2 to 6 and X is O or NH.

EXAMPLES

Example 1

Syntheses of Conjugates

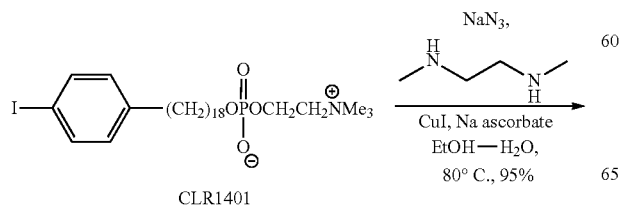

37
-continued

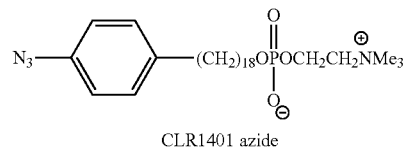
CLR1401 azide

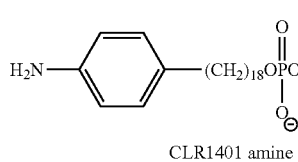
CLR1401 amine

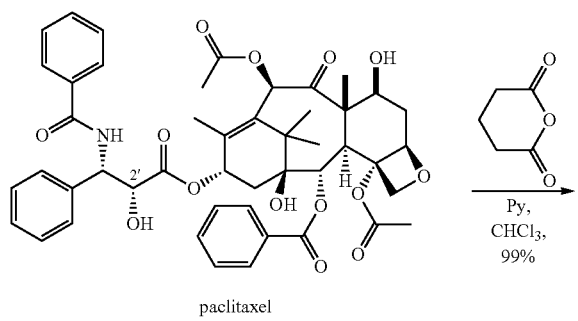
paclitaxel

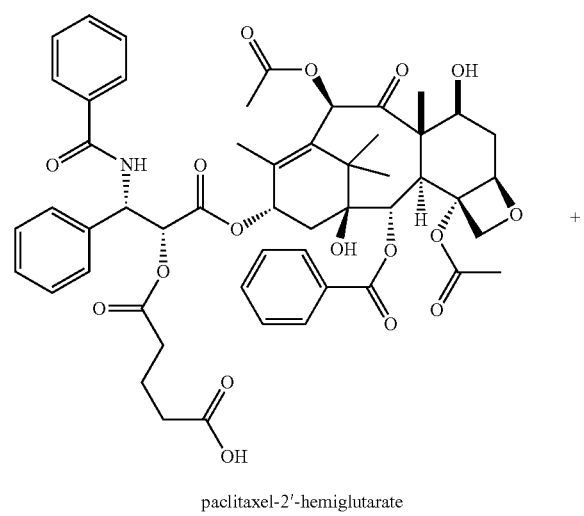
paclitaxel-2'-hemiglutarate

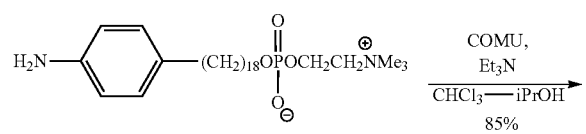

38
-continued

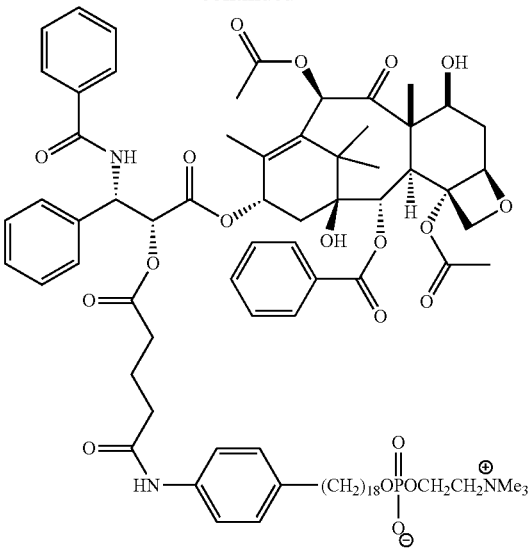
CLR1601

I. Synthesis of CLR1601

A. Synthesis of CLR1401 Azide 18-(p-Iodophenyl)octadecyl phosphocholine (4.01 g, 6.3 mmol), sodium azide (818 mg, 12.6 mmol) and sodium ascorbate (140 mg, 0.71 mmol) were dissolved in the mixture of degassed ethanol (28 ml) and water (12 ml) in the reaction vessel. Copper (I) iodide (120 mg, 0.63 mmol) and N,N'-dimethyl-ethylenediamine (0.1 ml, 0.94 mmol) were added to the reaction mixture. Reaction vessel was tightly closed and the mixture was stirred at 80° C. for 45 min. Reaction mixture was cooled to the room temperature, water (60 ml) was added, and the mixture was stirred for 30 min open to the air. The mixture was transferred to the separatory funnel, chloroform (80 ml) and methanol (52 ml) were added, and extraction was performed by shaking. Chloroform layer was removed, and extraction was repeated (2×80 ml of chloroform). Combined chloroform extracts were washed with 0.01 N HCl, dried over $Na_2SO_4$, filtered and evaporated to dryness. Residue was dissolved in chloroform (4 ml) and acetone (170 ml) was slowly added with stirring. The mixture was stirred for 30 min and filtered. The product was rinsed on the filter with acetone, and dried under high vacuum to give 3.31 g (95%) of 18-(p-azidophenyl)octadecyl phosphocholine.

B. Synthesis of CLR1401 Amine 18-(p-Azidophenyl)octadecyl phosphocholine (3.116 g) was placed in a Parr pressure bottle, methanol (30 ml) and catalyst 10% Pd/C (100 mg) were added. The hydrogenation reaction was performed under hydrogen pressure (55 psi) with shaking for 24 h. The bottle was depressurized, chloroform and methanol were added to dissolve some precipitated reaction product, and the mixture was filtered to remove the catalyst. Filtrate was evaporated to dryness and residue was dissolved in warm chloroform-methanol (1:1) mixture (10 ml). Hot acetone (150 ml) was added slowly with stirring, the mixture was cooled to the ambient temperature with stirring and filtered. Product was rinsed on the filter with acetone and dried under high vacuum. Yield of 18-(p-aminophenyl)octadecyl phosphocholine: 2.597 g (87%).

C. Synthesis of Paclitaxel-2'-Hemiglutarate

Paclitaxel (404 mg, 0.437 mmol) and glutaric anhydride (67 mg, 0.588 mmol) were dissolved in chloroform (8 ml) and pyridine (0.5 ml) was added. Reaction Mixture was stirred at room temperature for 24 h and evaporated to dryness. Residue was kept under high vacuum for 1.5 h to remove the residual pyridine. Crude product was purified by silica gel chromatography in chloroform-methanol (gradient from 98:2 to 95:5) to yield 452 mg (99%) of paclitaxel-2'-hemiglutarate.

D. Synthesis of CLR1601

Paclitaxel-2'-hemiglutarate (947 mg, 0.978 mmol) and 18-(p-aminophenyl)octadecyl phosphocholine (492 mg, 0.934 mmol) were suspended in chloroform (40 ml) and isopropanol (1.2 ml) mixture. To this suspension, trimethylamine (0.27 ml, 1.957 mmol) and COMU (419 mg, 0.978 mmol) were added. Reaction mixture was stirred at room temperature for 20 h by which time it became clear and homogeneous. Reaction mixture was transferred to a separation funnel and mixed with chloroform (40 ml), methanol (80 ml) and cold water (72 ml). Chloroform layer was removed, and extraction was repeated (2×80 ml of chloroform). Combined chloroform extracts were dried over $Na_2SO_4$, filtered and evaporated to dryness. The remaining residue was purified by chromatography on silica gel with chloroform-methanol (gradient from 9:1 to 5:5) followed by final elution with chloroform-methanol-water (65:25:4). After evaporation of the solvent, the product was dried under high vacuum to give 1.167 g (85%) of CLR1601.

II. Synthesis of CLR1602

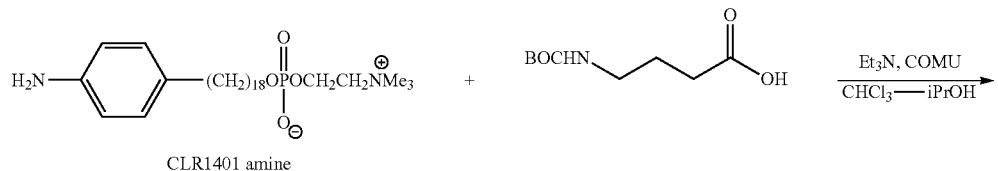

CLR1401 amine

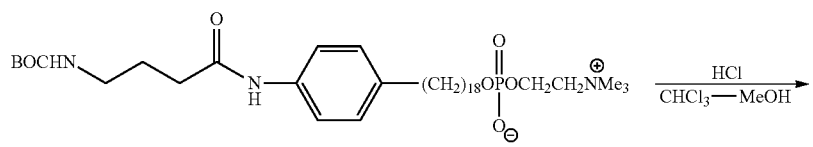

18-[p-(4-N-BOC-aminobutyramido)phenyl]octadecyl phosphocholine

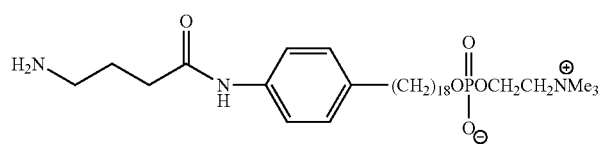

18-[p-(4-aminobutyramido)phenyl]octadecyl phosphocholine

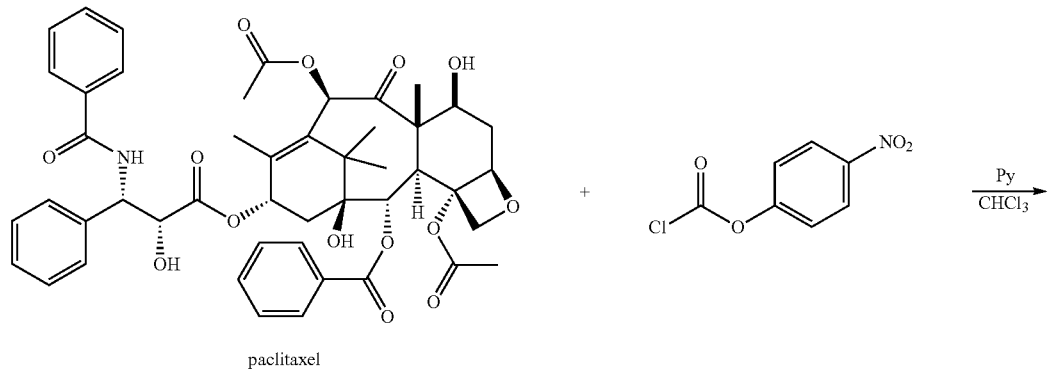

paclitaxel

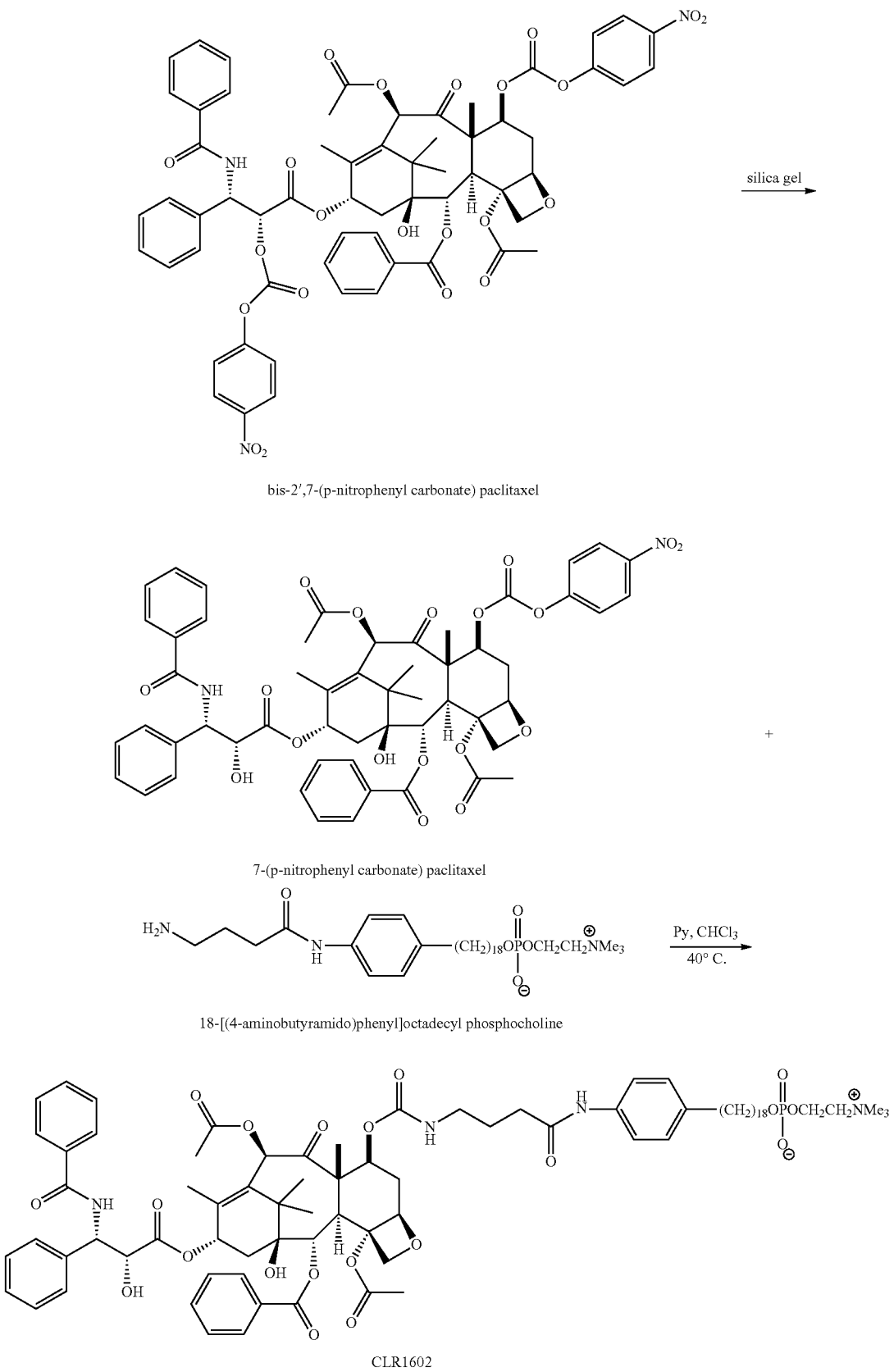

A. Synthesis of 18-[p-(4-N—BOC-aminobutyramido)phenyl]octadecyl phosphocholine 18-(p-Aminophenyl)octadecyl phosphocholine (76 mg, 0.144 mmol) and 4-N—BOC-aminobutyric acid (38 mg, 0.188 mmol) were suspended in chloroform (5 ml) and isopropanol (0.15 ml), then triethylamine (0.05 ml, 0.38 mmol) was added followed by COMU (80 mg, 0.188 mmol). Reaction mixture was stirred at room temperature for 24 h and quenched with 2 ml of saturated aqueous $NaHCO_3$ solution. Quenched reaction mixture was transferred into to a separation funnel and mixed with chloroform (35 ml), methanol (40 ml) and cold water (36 ml). Chloroform layer was removed, and extraction was repeated (2×40 ml of chloroform). Combined chloroform extracts were dried over $Na_2SO_4$, filtered and evaporated to dryness. Residue was purified by chromatography on silica gel with chloroform-methanol (gradient from 9:1 to 5:5) followed by final elution with chloroform-methanol-water (65:25:4). After evaporation of the solvent, the product was dissolved in warm chloroform-methanol mixture (1.5 ml) and precipitated with acetone. Product was collected by filtration and drying under high vacuum to give a white powder (100 mg, 97%).

B. Synthesis of 18-[p-(4-aminobutyramido)phenyl]octadecyl phosphocholine

18-[(4-N—BOC-aminobutyramido)phenyl]octadecyl phosphocholine (98 mg, 0.138 mmol) was dissolved in a mixture of chloroform (4 ml), methanol (2 ml) and concentrated HCl (0.2 ml). The reaction mixture was stirred overnight at ambient temperature and then was quenched by slow addition of the saturated aqueous $NaHCO_3$ solution (3 ml). Quenched reaction mixture was transferred into a separation funnel and mixed with chloroform (40 ml), methanol (40 ml) and cold water (36 ml). Chloroform layer was removed, and extraction was repeated (2×40 ml of chloroform). Combined chloroform extracts were dried over $Na_2SO_4$, filtered and evaporated to dryness. Product was purified by chromatography on silica gel with chloroform-methanol (100:65) followed by final elution with chloroform-methanol-conc. $NH_4OH$(aq) (100:65:15). After evaporation of the solvent, the product was dried under high vacuum to afford 50 mg (60%) of 18-[p-(4-aminobutyramido)phenyl]octadecyl phosphocholine.

C. Synthesis of 7-(p-nitrophenyl carbonate) paclitaxel

Paclitaxel (100 mg, 0.117 mmol) was dissolved in chloroform (4.5 ml), 8 drops of pyridine were added and the solution was cooled in an ice bath. Solid p-nitrophenyl chloroformate (200 mg, 1 mmol) was added in one portion. Reaction mixture was allowed to warm to ambient and was stirred for 24 h, then quenched with water (1 ml) and stirred for 15 min. The mixture was extracted with chloroform, the extract was washed with water, dried over $Na_2SO_4$, filtered and evaporated to dryness. Crude bis-2',7-(p-nitrophenyl carbonate) paclitaxel was dissolved in chloroform and loaded on the silica gel column. The crude product was left in the column for 72 h to complete hydrolysis of p-nitrophenyl carbonate at 2'-position. The column was eluted with dichloromethane-ethyl acetate (gradient from 98:2 to 90:10). After evaporation of the solvent, the product was precipitated with hexane and dried under high vacuum to provide 63 mg (53%) of 7-(p-nitrophenyl carbonate) paclitaxel. See. Arpicco S., et al., *Int J Pharm*, 2013, 454, 653-659.

D. Synthesis of CLR1602

7-(p-Nitrophenyl carbonate) paclitaxel (53 mg, 0.052 mmol) and 18-[p-(4-aminobutyramido)phenyl]octadecyl phosphocholine (47 mg, 0.077 mmol) were suspended in chloroform (2 ml) and pyridine (0.5 ml) and stirred at 40° C. for 5 h. The reaction mixture was evaporated to dryness, and residue was purified by chromatography on silica gel with chloroform-methanol (gradient from 9:1 to 5:5) followed by final elution with chloroform-methanol-water (65:25:4). After evaporation of the solvent, compound was dried under high vacuum to give 67 mg (86%) of solid CLR1602.

III. Synthesis of CLR1603

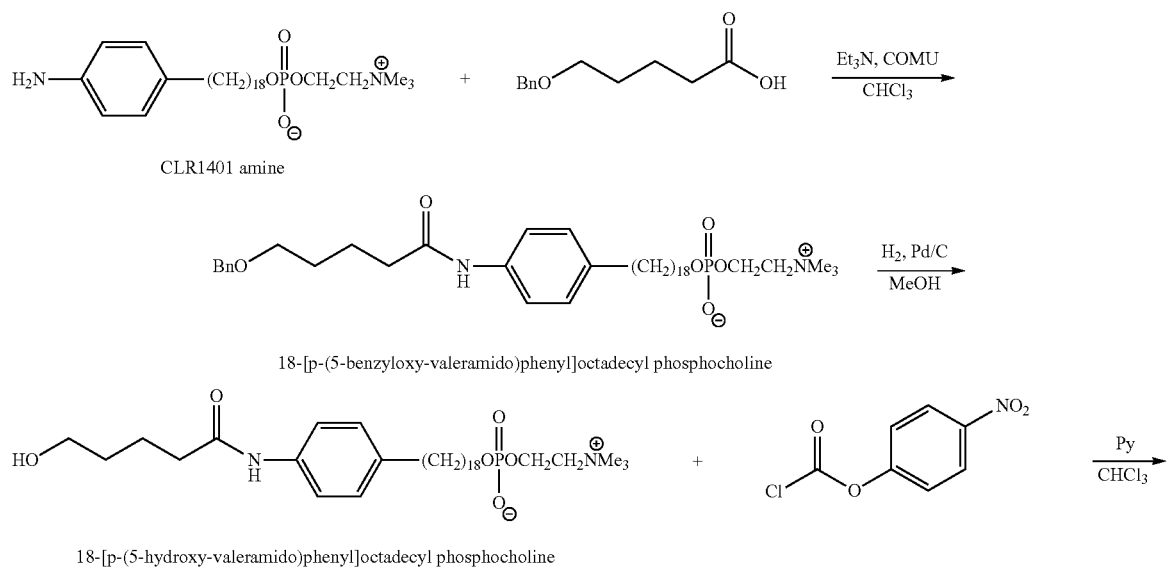

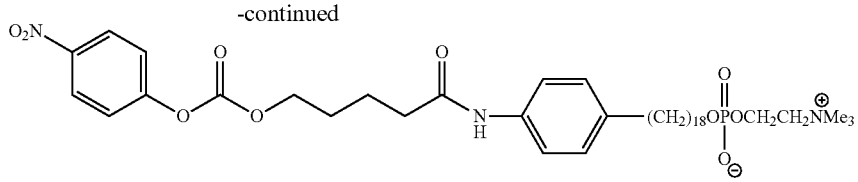

18-[p-(5-(p-nitro-phenoxycarbonyloxy)valeramido)phenyl]octadecyl phosphocholine

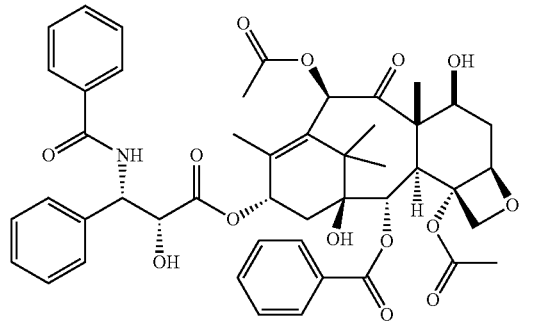

paclitaxel

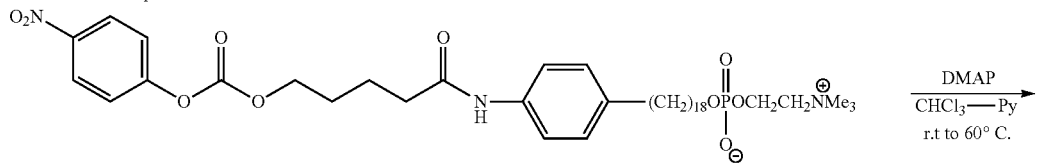

18-[p-(5-(p-nitro-phenoxycarbonyloxy)valeramido)phenyl]octadecyl phosphocholine $$\xrightarrow[\text{r.t to 60° C.}]{\text{DMAP} \atop \text{CHCl}_3\text{—Py}}$$

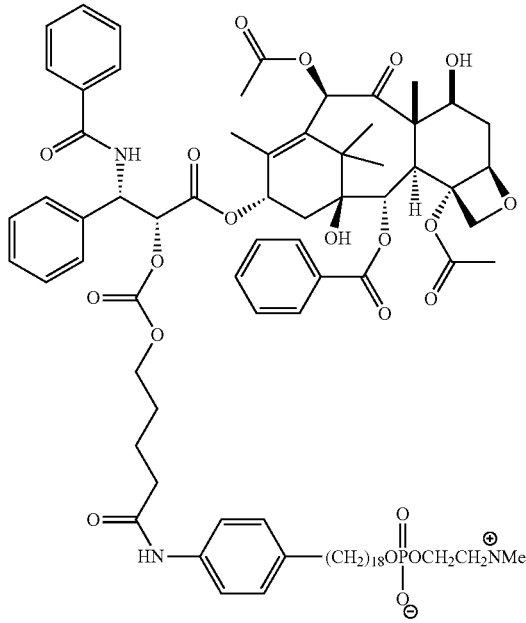

CLR1603

A. Synthesis of
18-[p-(5-benzyloxy-valeramido)phenyl]octadecyl phosphocholine 18-(p-Aminophenyl)octadecyl phosphocholine (760 mg, 1.443 mmol) and 5-benzyloxyvaleric acid (361 mg, 1.732 mmol; synthesized according to Can J Chem, 1992, 70, 1472-1445 and Org Lett, 2014, 16, 516-519) were suspended in chloroform (25 ml) and triethylamine (0.3 ml, 2.164 mmol) was added followed by solid COMU (741 mg, 1.732 mmol).

Reaction mixture was stirred at room temperature for 24 h and after completion, it was transferred into a separation funnel and mixed with chloroform (55 ml), methanol (80 ml) and cold water (72 ml). Chloroform layer was removed, and extraction was repeated (2×80 ml of chloroform). Combined chloroform extracts were dried over $Na_2SO_4$, filtered and evaporated to dryness. Residue was purified by chromatography on silica gel with chloroform-methanol (gradient from 9:1 to 5:5) followed by final elution with chloroform-methanol-water (65:25:3). After evaporation of the solvent and drying under high vacuum, the product was dissolved in warm chloroform-methanol mixture (3 ml) and hot acetone (75 ml) was slowly added with stirring. The mixture was cooled to the ambient temperature with stirring and filtered. Collected product was dried under high vacuum to give 18-[p-(5-benzyloxy-valeramido)phenyl]octadecyl phosphocholine (887 mg, 86%) as a white powder.

B. Synthesis of 18-[p-(hydroxy-valeramido)phenyl]octadecyl phosphocholine

18-[p-(5-Benzyloxy-valeramido)phenyl]octadecyl phosphocholine (868 g) was dissolved in methanol (15 ml), transferred into a Parr pressure bottle, and 10% Pd/C (75 mg) catalyst was added. The hydrogenation reaction was performed under hydrogen pressure (55 psi) with shaking for 24 h. The bottle was depressurized, and the mixture was filtered to remove the catalyst. Filtrate was evaporated to dryness and residue was dissolved in warm chloroform-methanol mixture (3-4 ml). Hot acetone (75 ml) was slowly added with stirring. The mixture was cooled to the ambient temperature with stirring and filtered. Collected product was dried under high vacuum to yield 18-[p-(5-hydroxy-valeramido)phenyl]octadecyl phosphocholine (718 mg, 95%) as a white powder.

C. Synthesis of 18-[p-(5-(p-nitro-phenoxycarbonyloxy)valeramido)phenyl]octadecyl phosphocholine 18-[p-(5-Hydroxy-valeramido)phenyl]octadecyl phosphocholine (40 mg, 0.064 mmol) and p-nitrophenyl chloroformate (25 mg, 0.124 mmol) were suspended in chloroform (3 ml) and pyridine (0.2 ml) was added. The reaction mixture was stirred for 24 h at room temperature. An additional portion of p-nitrophenyl chloroformate (15 mg) was added, and stirring was continued for another 1.5 h. Reaction was complete by TLC analysis. Reaction mixture was quenched with 1 ml of 1N HCl and transferred into the separation funnel with chloroform (20 ml), methanol (20 ml) and cold water (15 ml). Extraction was repeated (3×20 ml of chloroform). Combined chloroform extracts were dried over $Na_2SO_4$, filtered and evaporated to dryness. Residue was purified by chromatography on silica gel with chloroform-methanol (gradient from 9:1 to 5:5) followed by final elution with chloroform-methanol-water (65:25:4). After evaporation of solvent and precipitation with acetone, the residue was dried under high vacuum to give 48 mg (95%) of solid material.

D. Synthesis of CLR1603

Paclitaxel (46 mg, 0.054 mmol) and 18-[p-(5-(p-nitro-phenoxycarbonyloxy)valeramido)phenyl]octadecyl phosphocholine (43 mg, 0.054 mmol) were suspended in chloroform (2 ml) and pyridine (0.5 ml) in a reaction vial. DMAP (8 mg, 0.065 mmol) was added, the vial was tightly closed and the contents were stirred at 60° C. for 48 h. An additional quantity of paclitaxel (20 mg) was added, and the reaction was continued at 60° C. for another 48 h. Reaction mixture was concentrated, and residue was purified by silica gel chromatography with chloroform-methanol (gradient from 9:1 to 5:5) followed by final elution with chloroform-methanol-water (65:25:2) and (65:25:4). Evaporation of solvent and drying under high vacuum provided CLR1603 (50 mg, 62%).

IV. Synthesis of CLR1607

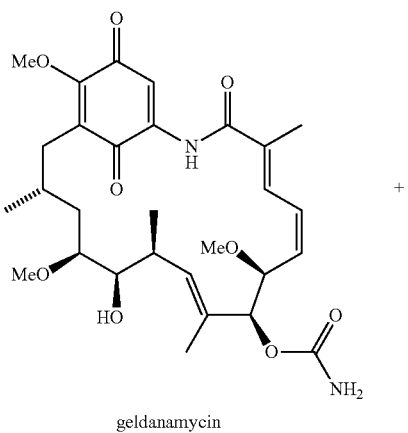

geldanamycin

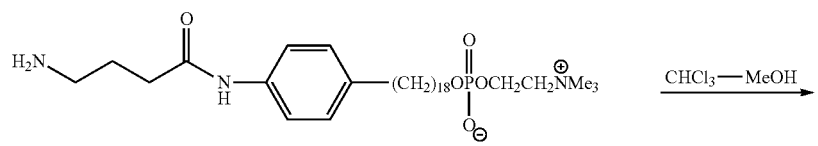

18-[p-(4-aminobutyramido)phenyl]octadecyl phosphocholine

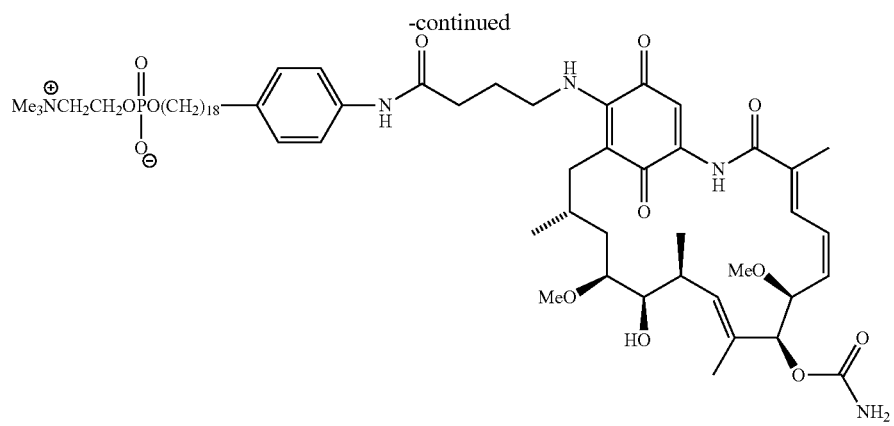

CLR1607

Geldanamycin (111 mg, 0.198 mmol) and 18-[p-(4-aminobutyramido)phenyl]octadecyl phosphocholine (110 mg, 0.18 mmol) were dissolved in chloroform (3.5 ml) and methanol (1 ml). One drop of triethylamine was added, and the reaction mixture was stirred at room temperature for 24 h. TLC showed about 80% completion of reaction. Additional geldanamycin (10 mg) was added, and stirring was continued for another 24 h. Reaction mixture was concentrated and residue purified by silica gel chromatography with chloroform-methanol (gradient from 9:1 to 5:5) followed by final elution with chloroform-methanol-water (65:25:2), (65:25:3) and (65:25:4). After evaporation of the solvent and drying under high vacuum, acetone was added and the mixture was evaporated. CLR1607 was obtained as a purple solid (174 mg, 85%).

Identity for each isolated product was confirmed by $^1$H-nmr and mass spectral analysis.

Examples 2 through 8 exhibit the ability of CLR1404 and related molecules to be sequestered and retained by various cancer types while simultaneously being eliminated from healthy tissue.

V. Synthesis of CLR1608

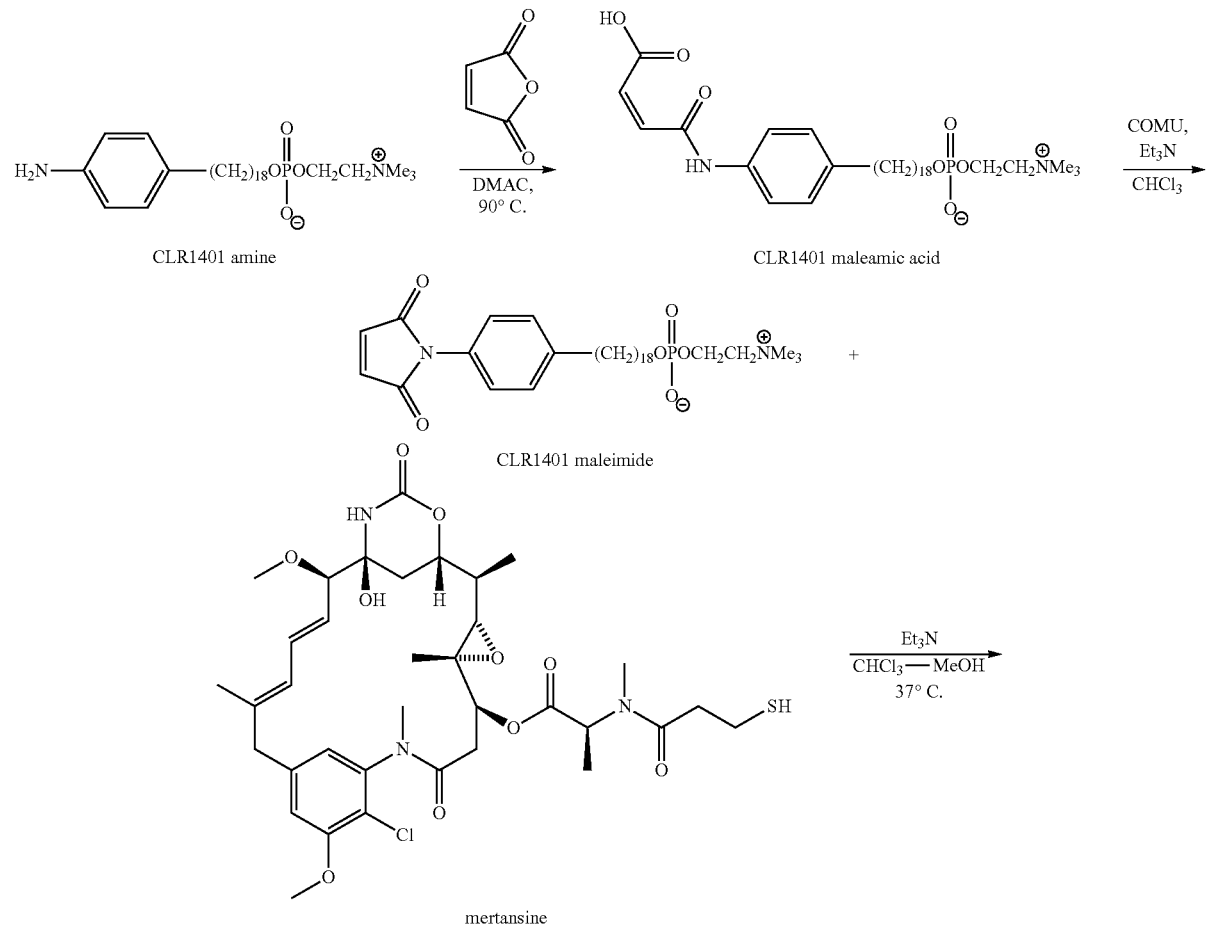

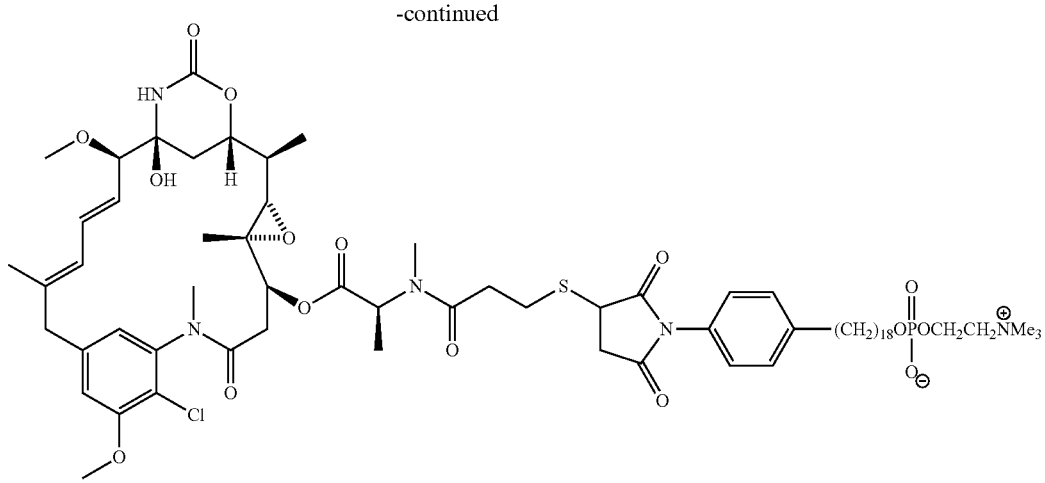

CLR1608

A. Synthesis of CLR1401 Maleamic Acid

CLR1401 amine (300 mg, 0.57 mmol) was dissolved in N,N-dimethylacetamide (12 ml) at 90° C. and maleic anhydride (61 mg, 0.627 mmol) was added in one portion. Reaction mixture was stirred at 90° C. for 1 h, cooled to the room temperature and stirred for 24 h. Acetone (25 ml) was slowly added with stirring, and the mixture was stirred at room temperature for 1 h. Precipitated product was filtered and rinsed on the filter with acetone, then dried under high vacuum. Yield: 327 mg (92%).

B. Synthesis of CLR1401 Maleimide

CLR1401 maleamic acid (100 mg, 0.16 mmol) was suspended in ethanol-free chloroform (5 ml), then triethylamine (0.05 ml, 0.352 mmol) and COMU (75 mg, 0.176 mmol) were added. The reaction mixture was stirred for 24 h, then transferred to a separation funnel and mixed with chloroform (40 ml), methanol (40 ml) and cold water (36 ml). Chloroform layer was removed, and extraction was repeated (2×40 ml of chloroform). Combined chloroform extracts were dried over $Na_2SO_4$, filtered and evaporated to dryness. The remaining residue was purified by chromatography on silica gel with chloroform-methanol (gradient from 9:1 to 5:5) followed by final elution with chloroform-methanol-water (65:25:4). After evaporation of the solvent, the product was precipitated with acetone, collected and dried under high vacuum to give 87 mg (90%) of CLR1401 maleimide.

C. Synthesis of CLR1608

CLR1401 maleimide (40 mg, 0.066 mmol) and mertansine (53 mg, 0.072 mmol) were dissolved in the mixture of chloroform (1.7 ml) and methanol (0.3 ml). Triethylamine (0.08 ml) was added, and the mixture was stirred at 37° C. for 24 h. The reaction mixture was concentrated, and residue was purified by chromatography on silica gel with chloroform-methanol (gradient from 9:1 to 5:5) followed by final elution with chloroform-methanol-water (65:25:3). After evaporation of the solvent, the product was dried under high vacuum to give 62 mg (70%) of CLR1608.

Example 2

CLR1501 is Preferentially Sequestered by Cancer Cells Via Lipid Rafts

Materials and Methods

PC-3 cells were pretreated with either 2 µg/ml filipin III or vehicle for 15 min, then washed and incubated with 2 µCi of $^{125}$I-CLR1404 for 1 h. The media was removed and the cells were washed with phosphate buffered saline containing 0.1% bovine serum albumin, trypsinized, then split into two samples for determination of cell number by DNA content ($A_{280}$ compared to a cell line specific standard curve) and counts per minute using a Gamma Counter (Perkin Elmer).
Results:
Pretreatment of PC-3 cells with filipin III, an agent that sequesters cholesterol and disrupts lipid rafts, resulted in nearly 40% less uptake of $^{125}$I-CLR1404 compared to untreated control cells (FIG. 1). This supports the hypothesis that CLR1404 uses lipid rafts as portals of entry into cancer cells. Notably, higher filipin III concentrations are cytotoxic, and therefore, complete lipid raft ablation (and presumably complete inhibition of CLR1404 analog uptake) could not be demonstrated.

Example 3

Preferential Uptake of CLR-1501 by Cancer Cells Over Healthy Cells

Materials and Methods

Human cancer cell lines were purchased from the American Type Culture Collection (ATCC). They included the following: Caki-2 (renal; clear cell carcinoma), HCT-116 (colorectal carcinoma); MES-SA/Dx5 (uterine sarcoma) [all maintained in McCoy's 5a medium supplemented with 10% fetal bovine serum (FBS)], Ovcar-3 (ovarian adenocarcinoma) [maintained in RPMI medium supplemented with 20% FBS], U87-MG (glioma) [maintained in minimum essential medium supplemented with 10% FBS], Mia Paca-2 (pancreatic carcinoma) (maintained in Dulbecco's modified Eagle's medium supplemented with 10% FBS), PC-3 (prostate carcinoma) (maintained in F-12K medium supplemented with 10% FBS), MDA-MB-231 (triple-negative mammary gland adenocarcinoma) (maintained in Leibovitz's medium supplemented with 10% FBS), and A549 (non-small cell lung carcinoma) (maintained in F-12 medium supplemented with 10% FBS). Normal human skin fibroblasts were purchased from ATCC and grown in Fibroblast Basal Medium PCS-201-030 supplemented with serum-free kit (Fibroblast Growth Kit-Serum-Free PCS-201-040). All media (except for MDA-MB-231 cell line) also contained penicillin (100 U/ml) and streptomycin (100 μg/ml) and were maintained at 37° C. with 5% $CO_2$ in air.

All cells were maintained at 37° C. in appropriate medium supplemented with 10% FBS and 5% $CO_2$. Before imaging, the cells were removed from flasks with 0.25% trypsin and were allowed to grow overnight on the microslides VI (Ibidi). The next day, the cells were washed with phosphate-buffered saline (PBS) and were incubated with either 5 or 7.5 μM (as indicated) of CLR1501 in appropriate serum-free medium for 24 hours. CLR1501 is a fluorescently labeled CLR1404 analog. CLR1501 was formulated with 0.4% of Polysorbate 20, 2% of ethanol, and saline. After washing thoroughly with PBS, the cells were imaged using Bio-Rad Radiance 2100 MP Rainbow laser scanning/multiphoton confocal microscope using a 1-s exposure time. Alternatively, cells were visualized using a Nikon AIR confocal microscope (Keck Laboratory, University of Wisconsin-Madison). The emission signal of CLR1501 was detected using Alexa Fluor 488 filters (ex/em 480/520 nm).

Figure 2:
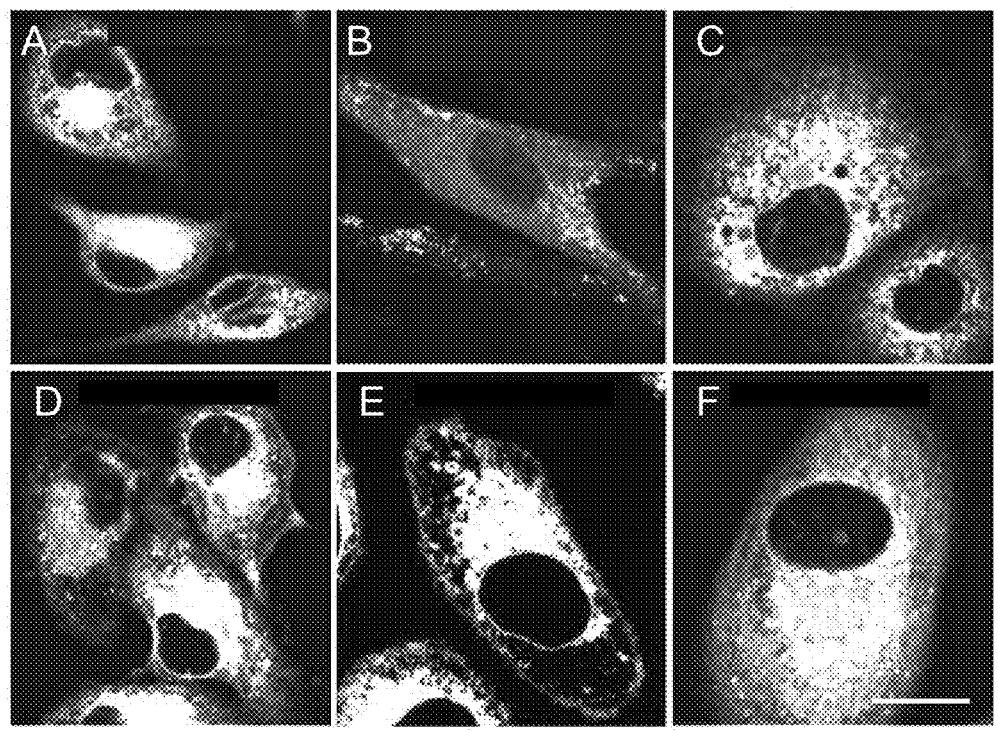
FIG. 2. Preferential uptake of CLR1501 by cancer cells. Compare uptake of CLR1501 by cancer cell lines in (A) and (C)-(F) with normal cells in (B). (A) Renal (Caki-2). (B) Normal human skin fibroblast. (C) Ovarian (OVcar-3). (D) Pancreatic (Panc-1). (E) Melanoma (A-375). (F) Prostate (PC-3).

Results:

CLR1501 was administered to five different cancer cell lines (renal, ovarian, pancreatic, melanoma, and prostate) and a normal human skin fibroblast line in vitro. Twenty-four hours later, CLR1501 exhibited from five to nine-fold preferential uptake in these cancer cell lines in vitro compared to normal fibroblasts (FIG. 2). Retained CLR1501 was associated with plasma and organelle membranes.

Example 4

Rat Glioma Model

Materials and Methods: All animals were housed and handled in accordance with the University of Wisconsin Research Animal Resources Center guidelines. Rat C6 glioma cells were propagated in DMEM medium (Life Technologies, Gaithersburg, Md.) supplemented with 10% heat-inactivated FBS (BioWhittaker, Walkersville, Md.), 100 U/ml penicillin G, 100 mg/ml streptomycin, and 0.01 M HEPES (Life Technologies, Gaithersburg, Md.). Intracranial tumor implantation was performed as described previously. Cohen J D, et al., Intracranial C6 glioma model in adult Wistar-Furth rats. *J Neuro Oncol* 1990 8(1):95-6. Briefly, $1 \times 10^6$ C6 cells were resuspended in 5 ml 1.2% methylcellulose and injected into the frontal lobes of anesthetized female Wistar rats (Harlan, Indianapolis, Ind.). Sham-operated animals received intracranial injections of an equal volume of methylcellulose without tumor cells.

Imaging Studies: Ten days after implantation, the presence of intracranial tumors was confirmed with MRI. Briefly, anesthetized rats (6) received 2 ml of Gadodiamide (Gd, Omniscan 287 mg/ml, Nycomed, Princeton, N.J.) intraperitoneally and imaged 10 min later using a 1.5 Tesla clinical MR system (GE Signa LX) and a GE phased array extremity coil. The T1-weighted (TR=500 ms, TE=16.5 ms) multislice sequences covering the entire brain of each rat were inspected to select tumor-bearing rats with varying tumor sizes, and sham-operated rats for NM404 injections.

NM404 [18-(4-iodophenyl)-octadecylphosphocholine] (100 mg) was radioiodinated with $^{125}$I via isotope exchange with $Na^{125}I$ in a melt of pivalic acid. Weichert, et al. *Int J Appl Rad Isotopes.* 1986; 37:907-913. NM404 has the same chemical structure as CLR1404 except that it is radioiodinated with $^{125}$I instead of $^{124}$I or $^{131}$I. Following HPLC purification NM404 was dissolved in an aqueous 2% Polysorbate 20 solution prior to tail vein injection (5-20 μCi/200 g rat) into four tumor-bearing and three sham-operated rats. At 1 (n=1), 2 (n=1), and 4 (n=2) days after NM404 injection, animals were euthanized ($CO_2$) and brains were excised and imaged on a modified Bioscan AR2000 radio-TLC scanner (1 mm increments at 2 min acquisition/lane and 1 mm high-resolution collimator). In addition, normal brain, blood, kidney, liver, spleen, thyroid, and tumor tissues were weighed, and radioactivity counted in a gamma counter. The tissue distribution of radioactivity was then correlated to brain histology.

Figure 4:
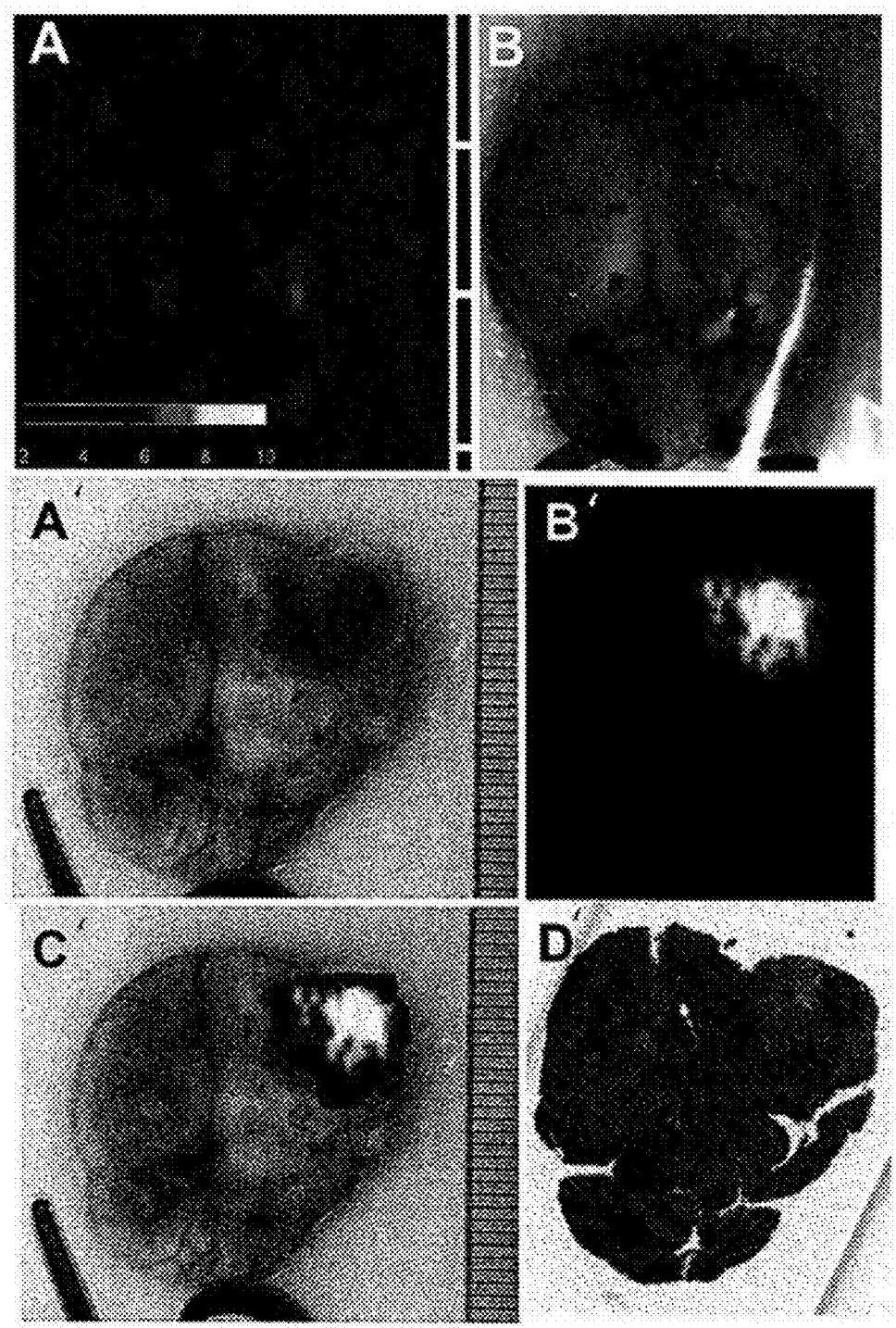
FIG. 4. Detection of C6-glioma in rat brain using $^{125}$I-NM404. (A) Bioscan of sham control rat brain. (B) Bioscan image of rat brain from (A) superimposed over digital photo showing background levels of $^{125}$I-NM404 in normal brain tissue. (A') Digital photo of C6-glioma bearing rat brain 4 days post $^{125}$I-NM404 injection. (B') Bioscan image of rat brain from (A'). (C') Position and size-matched images of (A') and (B') superimposed to show intense localization of NM404 in tumor. (D') H&E stained sample confirming presence of tumor.
Figure 5:
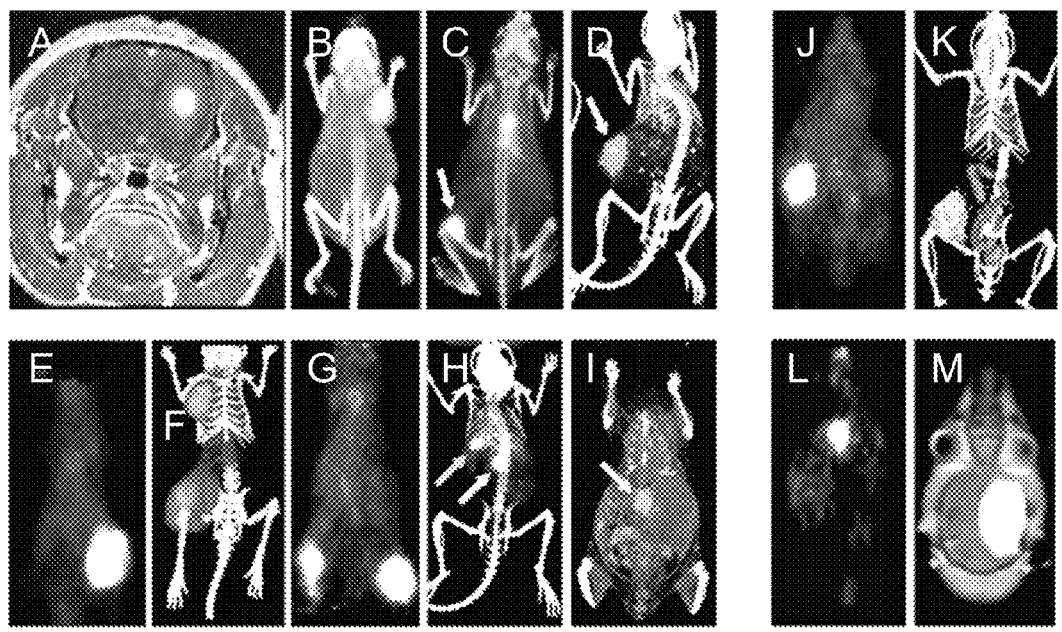
FIG. 5. $^{124}$I-CLR1404 uptake in a broad range of malignant tumors. (A)-(I) are rodent models with human cancer xenografts. (J)-(M) are rodent cancer models. (A) Orthotopic glioma U87 (rat). (B) Colon HCT-116. (C) Colon HT-29. Arrow indicates location of tumor. (D) Breast MDA-MB-231. Arrow indicates location of tumor. (E) Prostate PC-3. (F) Metastatic PC-3. (G) PC-3 tibial xenograft. (H) Pancreatic BxPC3. Lower arrow indicates location of tumor. Upper arrow indicates liver metastasis. (I) Ewing's sarcoma. Arrow indicates location of tumor. (J) Mouse SV40 bladder. (K) Mouse Breast 4T1. (L) Mouse pancreatic c-myc. (M) Rat brain CNS-1.

Results and Discussion: Initial imaging results with NM404 indicated striking uptake and prolonged retention in all gliomas ranging from 3-5 mm in diameter. Radioactivity in normal brain tissue was minimal in sham operated control animals (FIGS. 4A and 4B), whereas NM404 concentrated intensely in gliomas (FIG. 4A'-D'). Tumor to brain ratios (% injected dose/g) in C6 glioma-bearing rats were 10.5, 12.2, and 6.7 at 24, 48, and 96 h, respectively. As has been observed in previous cell culture and in vivo animal model studies, NM404 is apparently metabolized and eliminated from normal cells but becomes metabolically trapped in tumor cell membranes. Previous autoradiography experiments in other tumor models have suggested that only viable tumor cells, and not normal tissue or necrotic tissues, are capable of accumulating NM404. Interestingly, even small tumors measuring a few mm in diameter, were also detected after NM404 administration. These preliminary findings suggest that CLR1404 may also' be useful for visualization of small invasive tumor foci.

Conclusion:

As has been the case in all tumor models examined previously, NM404 displayed selective and prolonged retention by rat C6-gliomas evaluated in this study.

Example 5

$^{124}$I-CLR1404 Uptake in Various Malignant Tumors

Materials and Methods

All described animal studies were performed according to animal protocols approved by the Institutional Animal Care and Use Committee. Female athymic nude mice (Hsd:Athymic Nude-Foxn1nu or Crl:NU-Foxn1nu, Charles River Laboratories) about 4 to 5 weeks of age, 16 to 18 g (n=6), were used for human tumor xenograft studies. Mice were anesthetized with isoflurane and injected subcutaneously with viable tumor cells in 100 μl of Dulbecco's PBS (or, for glioma cells, 50 ml of PBS) into the right flank. Inoculum sizes were $1 \times 10^6$ (for renal, ovarian, glioma, pancreatic, prostate, and NSCLC models), $2 \times 10^6$ (for colorectal and uterine models), or $3 \times 10^6$ (breast).

Results:

Radioiodinated $^{124}$I-CLR1404 was tested in subcutaneous and orthotopic xenografts of 60 different spontaneous, transgenic, human, and rodent malignant cell lines and tumor types. After intravenous administration, $^{124}$I-CLR1404 localized in almost all primary and metastatic malignant tumors regardless of anatomic location. Representative examples are of both human (FIG. 5A-5I) and rodent (FIG. 5J-M) tumors.

TABLE 1

Uptake of $^{124}$I-CLR1404 in a Broad Range of Cancer Types

| | Tumor model | Species | Category | Uptake* |
|---|---|---|---|---|
| 1 | Prostate PC-3 | SCID mouse | Adenocarcinoma | Yes |
| 2 | Lung A-549 (NSCLC) | SCID mouse | Adenocarcinoma | Yes |
| 3 | Lung NCI H-69 (Oat Cell) | SCID mouse | Small cell carcinoma | Yes |
| 4 | Adrenal H-295 | SCID mouse | Adenocarcinoma | Yes |
| 5 | Adrenal RL-251 | SCID mouse | Adenocarcinoma | Yes |
| 6 | Colon-51 | SCID mouse | Adenocarcinoma | Yes |
| 7 | Colon LS180 | SCID mouse | Adenocarcinoma | Yes |
| 8 | Colon DLD1 | SCID mouse | Adenocarcinoma | Yes |
| 9 | Colon HT-29 | SCID mouse | Adenocarcinoma | Yes |
| 10 | Colon LS-180 | Nude mouse | Adenocarcinoma | Yes |
| 11 | Glioblastoma U87 | Nude mouse and NOD-SCID | Glioma | Yes |
| 12 | Melanoma A-375 | Nude mouse | Adenocarcinoma | Yes |
| 13 | Multiple myeloma MM.1S | Nude mouse | Myeloma | Yes |
| 14 | Neuroblastoma SK-N-AS | Nude mouse | Neuroblastoma | Yes |
| 15 | Neuroblastoma NB1691 | Nude mouse | Neuroblastoma | Yes |
| 16 | Neuroblastoma CHLA-20 | Nude mouse | Neuroblastoma | Yes |
| 17 | Neuroblastoma Lan5 | Nude mouse | Neuroblastoma | Yes |
| 18 | Ovarian HTB-77 | Nude mouse | Adenocarcinoma | Yes |
| 19 | Ovarian Ovcar-3 | Nude mouse | Adenocarcinoma | Yes |
| 20 | Pancreatic BXPC3 | Nude mouse | Adenocarcinoma | Yes |
| 21 | Pancreatic Mia Paca-2 | Nude mouse | Carcinoma | Yes |
| 22 | Pancreatic Capan-1 | Nude mouse | Adenocarcinoma | Yes |
| 23 | Renal cell Caki-2 | Nude mouse (orthotopic) | Clear cell carcinoma | Yes |
| 24 | Renal cell ACHN | Nude mouse (orthotopic) | Adenocarcinoma | Yes |
| 25 | Sarcoma (Meth-A) | Nude mouse | Fibrosarcoma | Yes |
| 26 | Head and neck SCC1 | Nude mouse | Squamous cell carcinoma | Yes |
| 27 | Head and neck SCC6 | Nude mouse | Squamous cell carcinoma | Yes |
| 28 | Prostate LNCap | Mouse | Adenocarcinoma | Yes |
| 29 | Prostate LuCap | Mouse | Adenocarcinoma | Yes |
| 30 | Breast MCF-7 | Rat | Adenocarcinoma | Yes |
| 31 | Triple negative breast MDA-MB231 | Nude mouse | Adenocarcinoma | Yes |
| 32 | Uterine MES SA/Dx5 | Nude mouse | Sarcoma | Yes |
| 33 | Glioblastoma 22 GSC | NOD-SCID mouse (orthotopic) | Glioma | Yes |
| 34 | Glioblastoma 105 GSC | NOD-SCID mouse (orthotopic) | Glioma | Yes |
| 35 | Breast 4T1 | Endogenous mouse (orthotopic) | Adenocarcinoma | Yes |
| 36 | Bladder SV40 | Mouse (orthotopic) | Adenocarcinoma | Yes |
| 37 | Prostate MatLyLu | Rat | Adenocarcinoma | Yes |
| 38 | Walker256 | Rat | Carcinosarcoma | Yes |
| 39 | TRAMP prostate | Endogenous mouse | Adenocarcinoma | Yes |
| 40 | Colon CT26 | SCID mouse | Adenocarcinoma | Yes |
| 41 | Colon Pirc | Autochthonous Pirc rat | Adenocarcinoma | Yes |
| 42 | Min mouse intestinal | Endogenous mouse | Adenocarcinoma | Yes |
| 43 | Melanoma | Mouse | Adenocarcinoma | Yes |
| 44 | Mammary SCC | ApcMin/+ mouse | Squamous cell carcinoma | Yes |
| 45 | Mammary AC | ApcMin/+ mouse | Adenocarcinoma | Yes |
| 46 | Hepatocellular carcinoma | Endogenous mouse | Adenocarcinoma | Yes |
| 47 | Glioma L9 | Rat xenograft | Glioma | Yes |
| 48 | Glioma C6 | Rat xenograft | Glioma | Yes |
| 49 | Glioma CNS1 | Rat xenograft | Glioma | Yes |
| 50 | Glioma RG2 | Rat xenograft | Glioma | Yes |
| 51 | Retinoblastoma | Endogenous mouse | Blastoma | Yes |
| 52 | Pancreatic c-myc | Endogenous mouse | Adenocarcinoma | Yes |
| 53 | Pancreatic Kras | Endogenous mouse | Adenocarcinoma | Yes |
| 54 | Cervical-HPV | Endogenous mouse | Adenocarcinoma | Yes |
| 55 | Esophageal | Endogenous Mouse | Adenocarcinoma | Yes |
| 56 | Intestinal polyp | Endogenous mouse | Adenoma (benign) | No |
| 57 | Mammary alveolar hyperplasia | Endogenous mouse | Hyperplasia (benign) | No |
| 58 | Hepatoma Hep-3B | Nude mouse | Carcinoma | No |
| 59 | Hepatoma Hep-G2 | Nude mouse | Carcinoma | No |
| 60 | Pirc rat colon adenoma | Pirc rat | Adenoma | No |

*Tumor uptake was considered positive if tumor to muscle ratio was greater than 3.
Tumor: muscle ratio less than or equal to 2 was considered negative.

Example 6

Clinical Trial Evaluating Patients with Non-Small Cell Lung Carcinoma ("NSCLC") Using CLR1404

Figure 6:
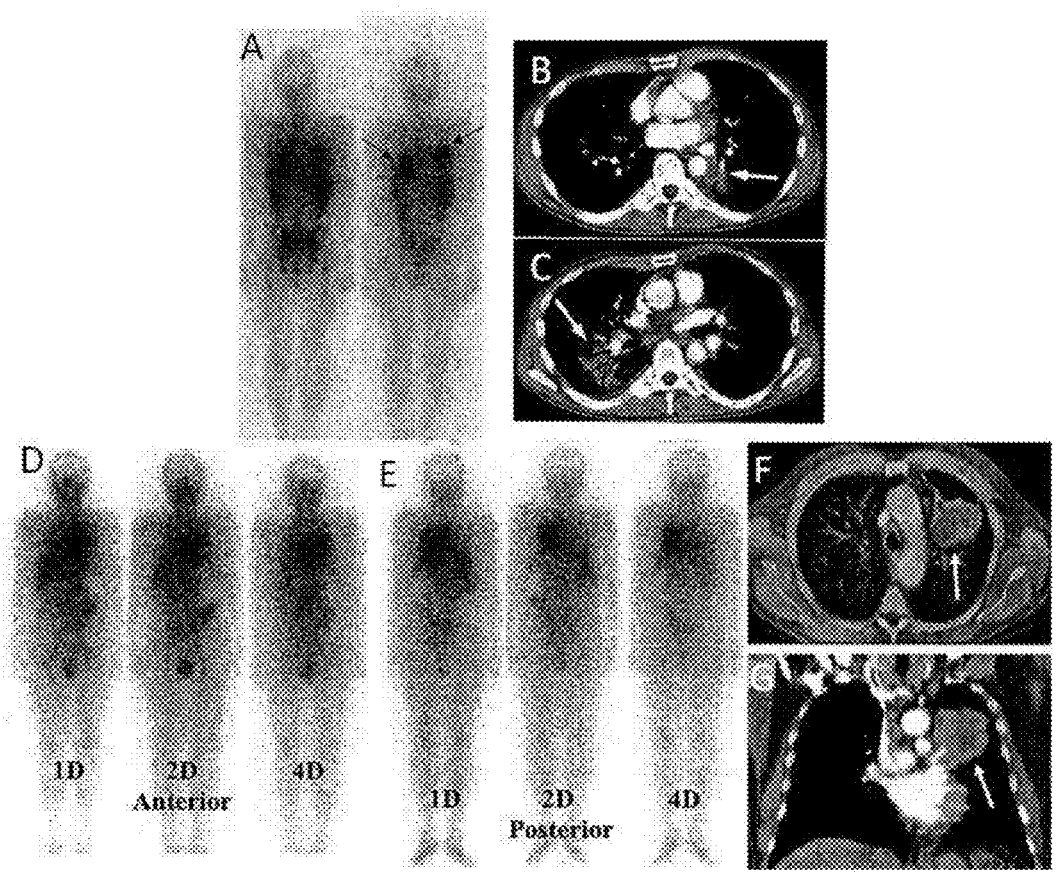
FIG. 6. Detection of non-small cell lung cancer ("NSCLC") tumors in human patient using $^{131}$I-CLR1404. (A) shows gamma camera images of Patient 1 at 4 and 11 days post $^{131}$I-CLR1404 injection. Note intense and prolonged retention of CLR1404 in the NSCLC tumors (arrows). (B and C) show the location and size of focal 3 cm lesion in left lung (A) and large infiltrative mass in right lung (B) (arrows). (D and E) show whole body planar nuclear medicine images of Patient 2 1, 2 and 4 days post $^{131}$I-CLR1404 IV administration. (F and G) show axial (F) and coronal (G) CT scans indicating location of large 6 cm NSCLC tumor (arrows).

Although CLR1404 has displayed selective and prolonged tumor retention in 55/60 xenograft and spontaneous rodent models, a physician sponsored IND initiated clinical evaluation of the agent in Stage 4 human NSCLC patients in order to determine whether or not it would exhibit similar tumor uptake and retention properties in humans. To date, two patients with advanced NSCLC were imaged after an injection of <1 mCi of $^{131}$I-CLR1404. Blood and urine samples were collected at predetermined times, and gamma imaging performed at several time points following administration. In both patients, significant tumor uptake and retention of CLR1404 was demonstrated in the primary lung tumor, as seen in FIG. 6. Relative to the high liver uptake values seen previously with its first generation predecessor, NM324, liver and abdominal activity are much lower with CLR1404, suggesting the feasibility of evaluating this agent in other abdominal cancers including pancreatic, colon, and prostate.

Materials and Methods: Following intravenous injection of iodine-131 labeled CLR1404 (1 mCi/20 µg), patients with advanced NSCLC where scanned at 3, 6, 24, 48, 96 h and at 7 and 11 days on a GE Maxxus dual Head SPECT scanner. Blood and urine samples were collected for pharmacokinetic analysis as well as clinical hematologic, renal, and hepatic bioanalysis.

Results: Initial qualitative imaging results indicate that iodine-131 labeled CLR1404 clearly localizes in bilateral pulmonary masses as early as 24 h after injection and is selectively retained in these tumors in excess of 11 days. Moreover, background radioactivity in the liver and lower abdominal region including urinary bladder, kidneys, and intestines was significantly less than was observed previously with its predecessor, NM324. No adverse reactions were observed in any of the patients.

Conclusions: These preliminary findings suggest that CLR1404 exhibits similar tumor uptake and retention properties in human NSCLC as was seen previously in rodent models. Although based on only two patients at this point, it appears that CLR1404 does indeed localize in and undergo selective and prolonged tumor retention in human non-small cell lung, cancer.

Patient 1: 55 year old male with bilateral 3 cm left lobe and infiltrative right lobe NSCLC and a brain metastasis and a small right adrenal mass. He has participated in numerous standard and experimental treatment regimens. Images are shown in FIG. 6A-C.

Patient 2: 70 year old male recently diagnosed with 6 cm upper lobe non-small cell lung carcinoma, a 5 cm liver mass, an iliac bone metastasis and a very small brain metastasis. He had recently completed low dose carboplatin/taxol chemotherapy and palliative radiotherapy to the iliac and brain metastases the week prior to initiating the CLR1404 trial. Images are shown in FIG. 6D-G.

Example 7

Detection of 3 Previously Unknown Brain Tumor Metastases in NSCLC Patient Using $^{124}$I-CLR1404

Materials and Methods

Human PET brain scans were acquired on a 64-slice PET/CT scanner (Discovery VCT, General Electric) at multiple time points after the injection of about 5 mCi of $^{124}$I-CLR1404 using a 90-min dynamic acquisition sequence (2D, nine frames at 10 min each, VIP list mode on) and reconstructed [Advantage Workstation version AW4.4, General Electric, 30 cm DFOV (display field of view), 128×128, OSEM VUE Point, 10 subsets with two iterations, standard z axis, attenuation correction and dead time, scatter, and decay correction].

Figure 7:
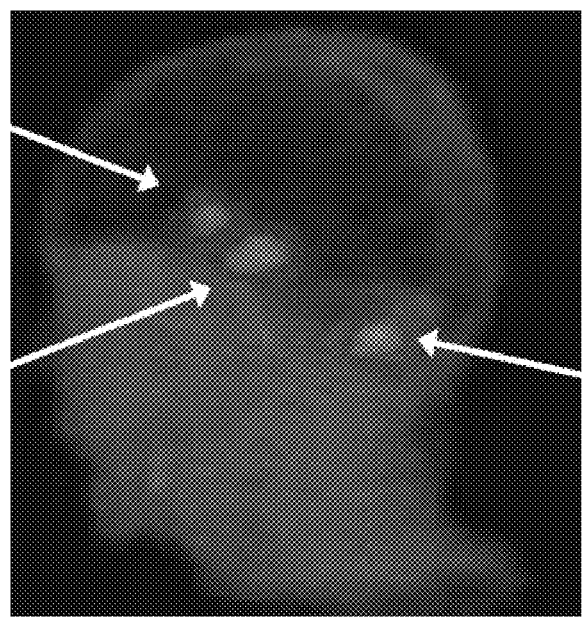
FIG. 7. Detection of 3 previously unknown brain tumor metastases in NSCLC patient using $^{124}$I-CLR1404. Arrows indicate location of tumors as imaged using PET/CT after uptake of $^{124}$I-CLR1404 by cancer cells.

Results:

Preliminary results were obtained in an NSCLC patient without neurological symptoms using $^{124}$I-CLR1404 PET/CT. Imaging revealed three previously unknown brain lesions highly suspicious for metastases that were subsequently confirmed with gadolinium-enhanced MRI (FIG. 7).

Example 8

Detection of Tumor Recurrence of a Right Frontal Falcine Metastasis Using CLR1404

Figure 8:
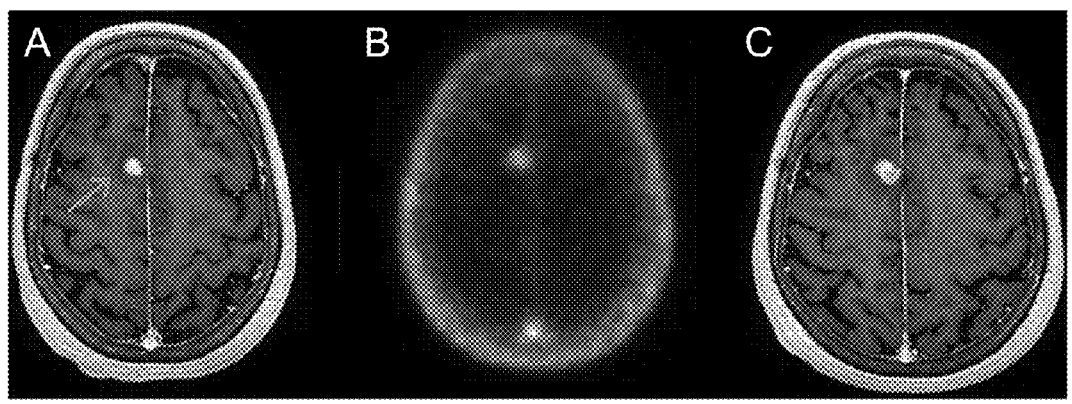
FIG. 8. Detection of tumor recurrence of a right frontal falcine metastasis using $^{124}$I-CLR1404. (A) MRI of brain following radiosurgery. Arrow indicates lesion which was interpreted as radiation necrosis. (B) PET image using $^{124}$I-CLR1404 shows uptake of $^{124}$I-CLR1404 by lesion. (C) MRI of brain 8 months after stereotactic radiosurgery shows increase in size of lesion indicating possible recurrence.
Figure 9:
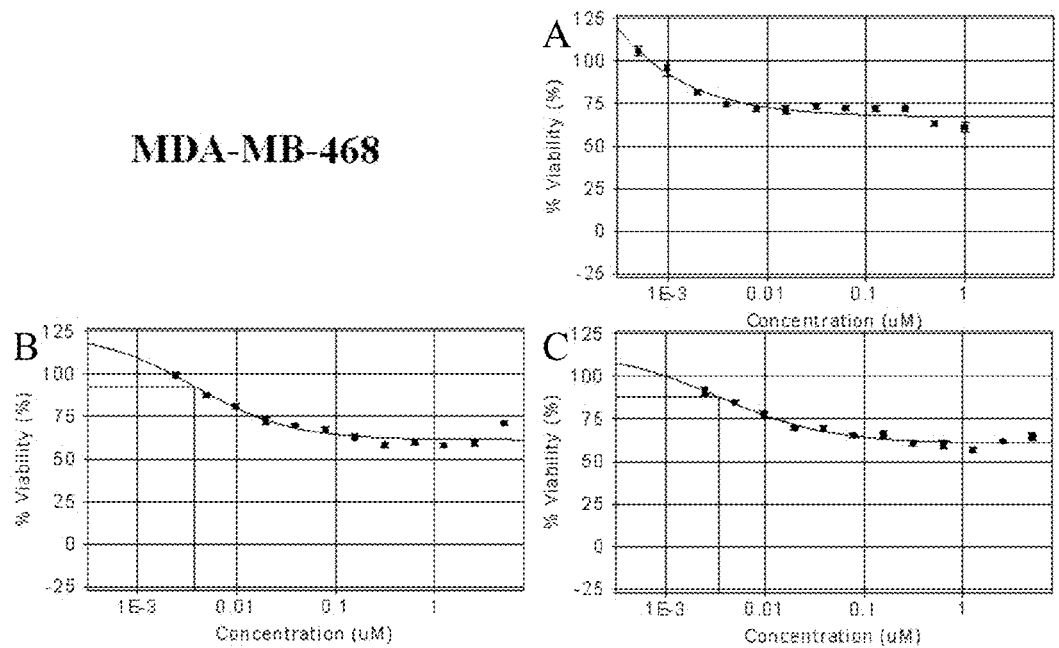
FIG. 9. PLE-Paclitaxel Conjugates IC$_{50}$ for MDA-MB-468. (A) free paclitaxel, (B) CLR1601 and (C) CLR1603.
Figure 10:
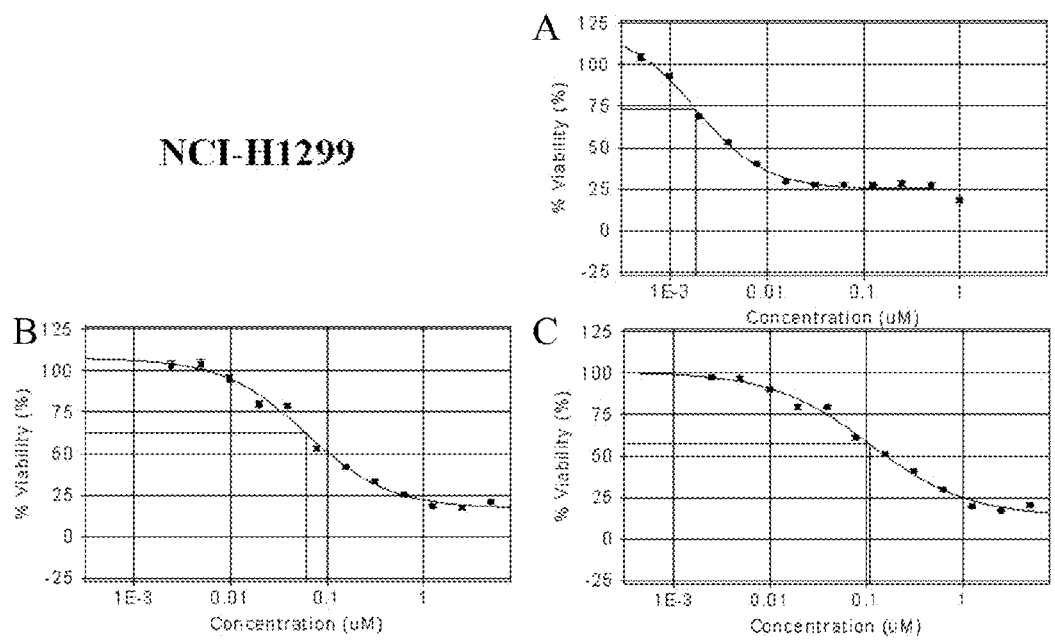
FIG. 10. PLE-Paclitaxel Conjugates IC$_{50}$ for NCI-H1299. (A) free paclitaxel, (B) CLR1601 and (C) CLR1603.
Figure 11:
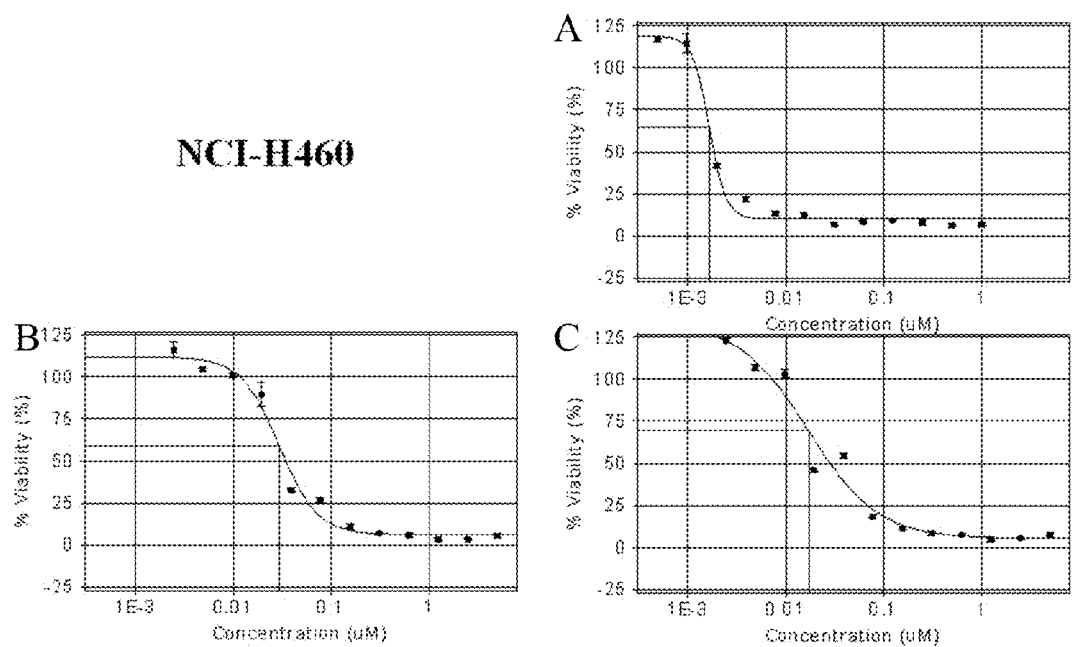
FIG. 11. PLE-Paclitaxel Conjugates IC$_{50}$ for NCI-H460. (A) free paclitaxel, (B) CLR1601 and (C) CLR1603.
Figure 12:
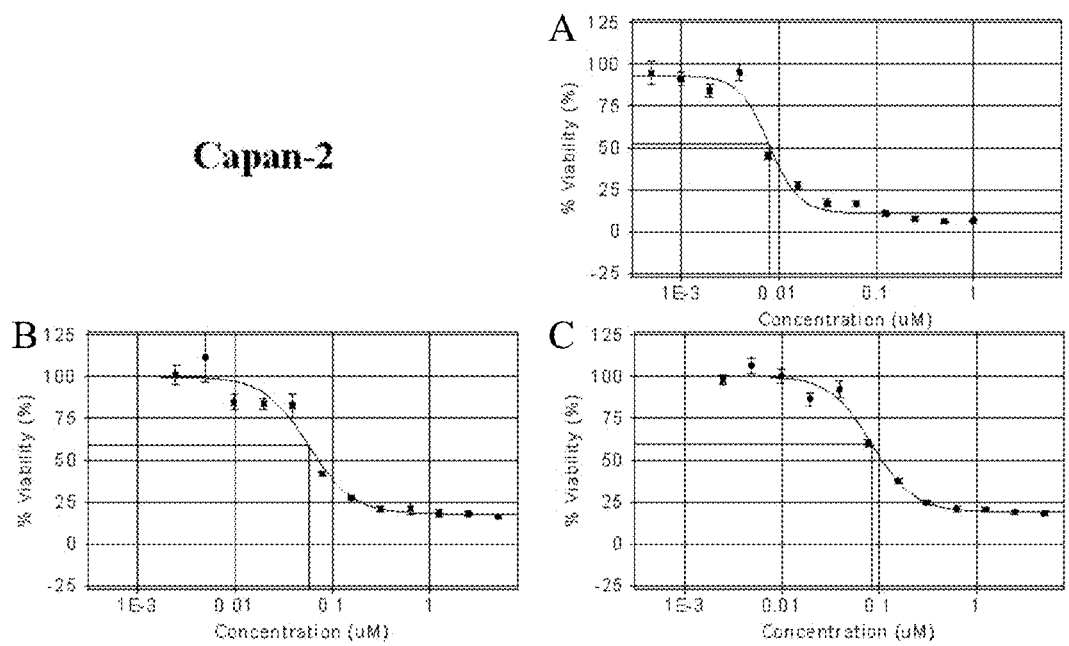
FIG. 12. PLE-Paclitaxel Conjugates IC$_{50}$ for Capan-2. (A) free paclitaxel, (B) CLR1601 and (C) CLR1603.
Figure 13:
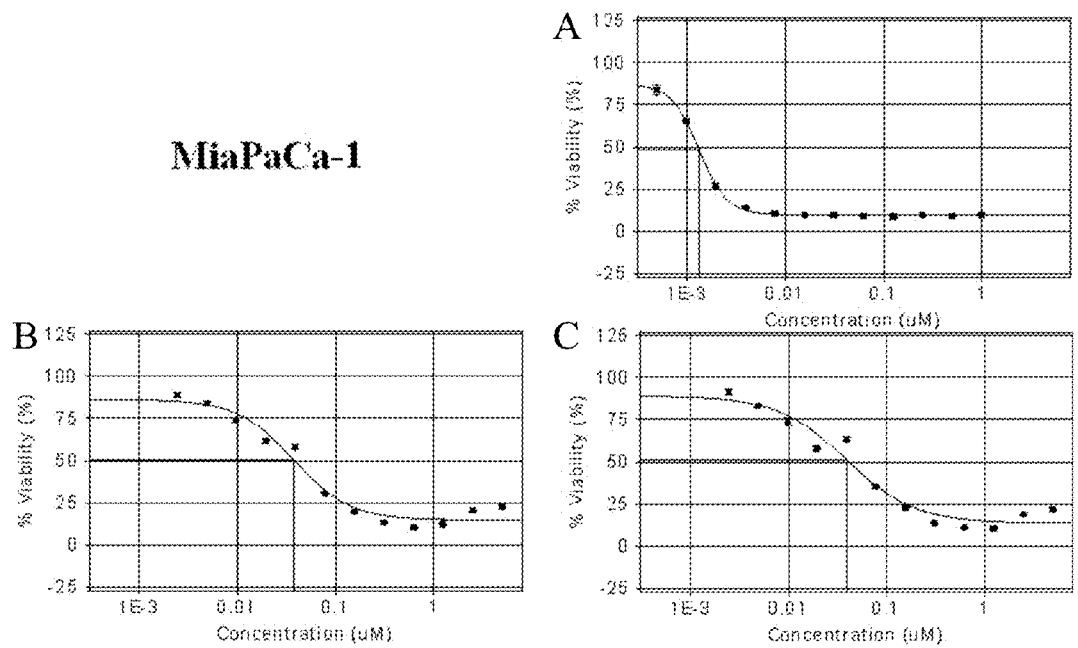
FIG. 13. PLE-Paclitaxel Conjugates IC$_{50}$ for MiaPaCa-1. (A) free paclitaxel, (B) CLR1601 and (C) CLR1603.
Figure 14:
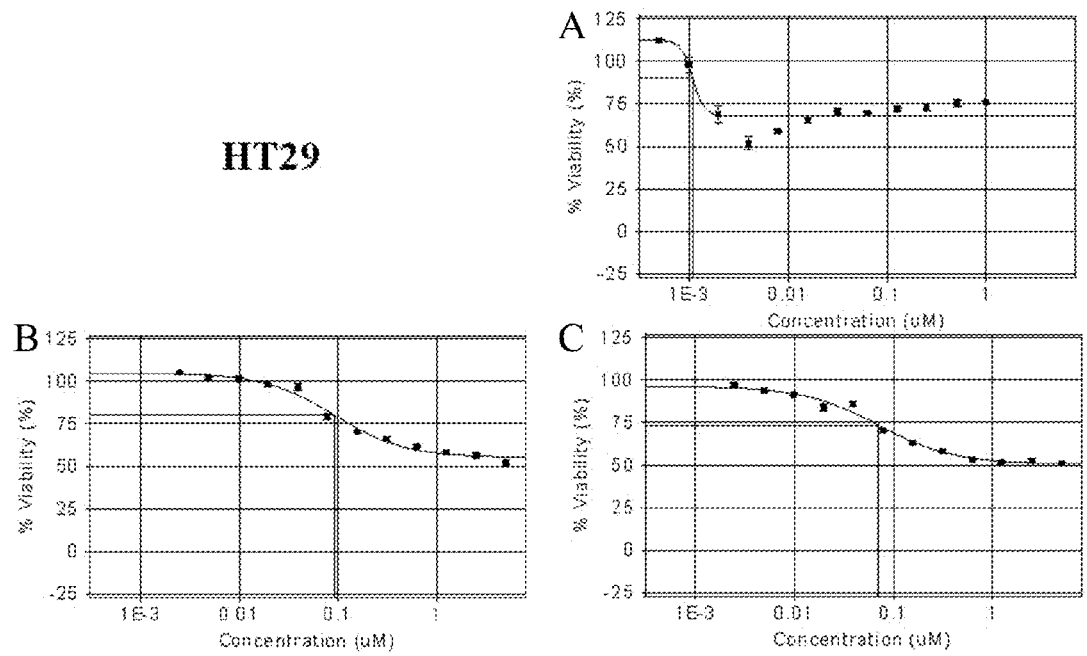
FIG. 14. PLE-Paclitaxel Conjugates IC$_{50}$ for HT29. (A) free paclitaxel, (B) CLR1601 and (C) CLR1603.
Figure 15:
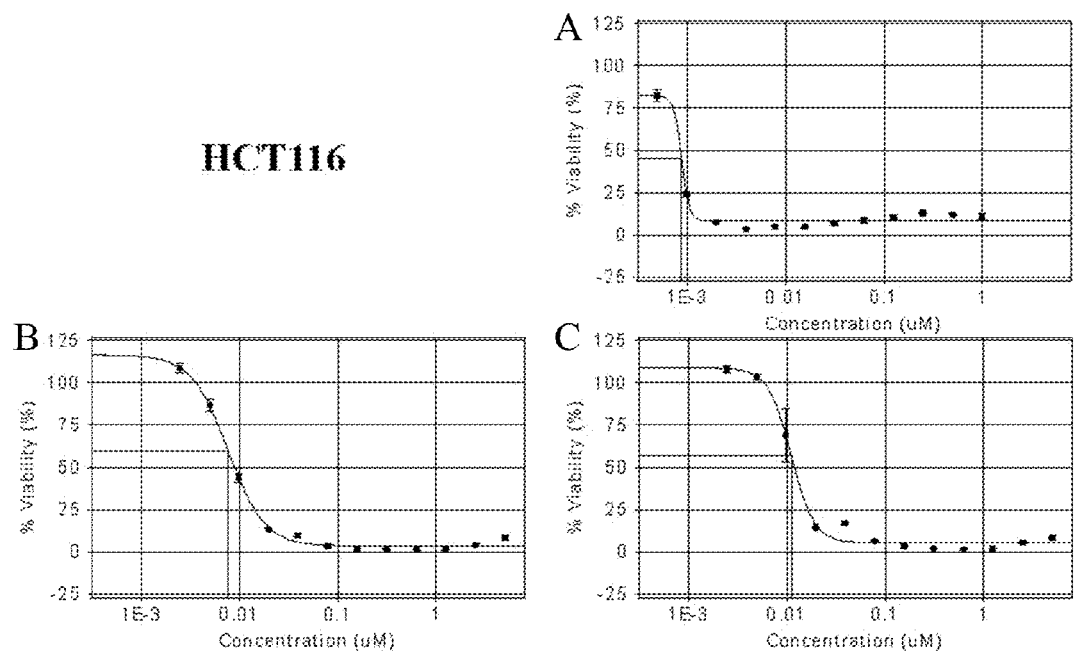
FIG. 15. PLE-Paclitaxel Conjugates IC$_{50}$ for HCT116. (A) free paclitaxel, (B) CLR1601 and (C) CLR1603.
Figure 16:
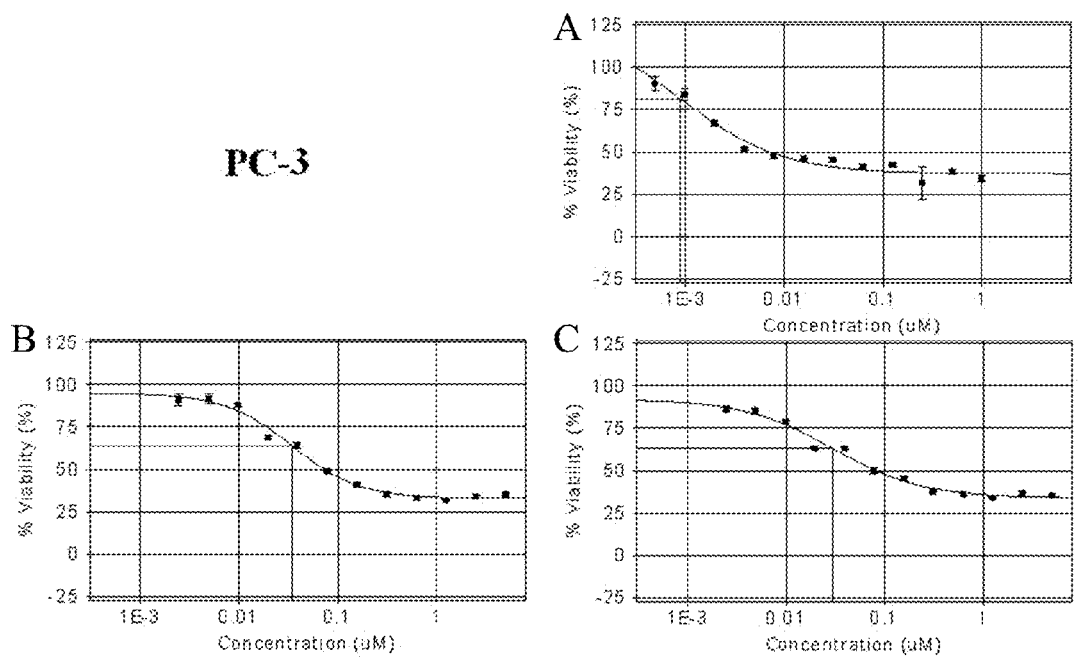
FIG. 16. PLE-Paclitaxel Conjugates IC$_{50}$ for PC-3. (A) free paclitaxel, (B) CLR1601 and (C) CLR1603.

Recurrent brain metastasis in 60-year-old woman with malignant melanoma. Magnetic resonance ("MR") (FIG. 8A) and $^{124}$I-CLR1404 PET images (FIG. 8B) and images 8 months after stereotactic radiosurgery for tumor recurrence of a right frontal falcine metastasis (FIG. 8C) shows a focus of abnormal activity with CLR1404 (arrow). Corresponding enhancing focus on initial MR imaging was interpreted as radiation necrosis versus possible recurrence. Subsequent MR imaging showed further increase in size of the nonspecific enhancing lesion, coupled with increased perilesional edema indicating a recurrence of the malignant tumor. These results indicate that $^{124}$I-CLR1404 was sequestered by cancer cells that were resistant to the radiosurgery and eventually established a recurrent tumor.

Compounds of the present invention include anti-cancer drugs linked to the CLR1404 core molecule. These compounds are capable of targeting cancer cells and cancer stem cells including brain cancer cells such that the anti-cancer drug is sequestered and retained by the cancer cell. These compounds provide the first targeted treatment of cancer capable of being adapted to specifically administer a range of anti-cancer drugs to cancer cells to both treat the cancer and prevent metastasis and recurrence.

Example 9

Paclitaxel-Conjugates and IC50 for Various Cancer Cell Lines

Method

Cancer cell lines including, MDA-MB-468 (Breast), NCI-H1299 (Lung), NCI-H460 (Lung), Capan-2 (Pancreas), MiaPaCa-1 (Pancreas), HT29 (Colorectal), HCT116 (Colorectal) and PC-3 (Prostate) were treated with serial concentrations of paclitaxel and CLR1404-paclitaxel conjugates (i.e. CLR1601, CLR1602 and CLR1603). The cell lines were then measured for cell viability and reported as IC50 for each treatment.

Results

CLR1601 and CLR1603 were capable of reducing cell viability for each of MDA-MB-468 (Breast), NCI-H1299 (Lung), NCI-H460 (Lung) Capan-2 (Pancreas), MiaPaCa-1 (Pancreas), HT29 (Colorectal), HCT116 (Colorectal) and PC-3 (Prostate) cancer cell lines. See FIGS. 9-16, respectively. IC50 for each paclitaxel-1404 conjugate (i.e. CLR1601 and CLR1603) and paclitaxel are reported in Table 2. IC50 for CLR1602 is not shown, however CLR1602 was not capable of significantly reducing cancer cell line viability because CLR1602 is non-hydrolyzable. In vivo, free paclitaxel is taken up by cancerous tumor cells at a much lower rate due to the non-specific nature of paclitaxel uptake. Thus, in vivo, the amount of PLE-paclitaxel conjugate necessary for cancer cell death should be on par or less than that for paclitaxel and may result in a greatly reduced toxicity to non-cancer cells.

TABLE 2

IC50 for CLR1601, CLR1603 and Paclitaxel

| | CLR1601 | CLR1603 | Paclitaxel |
|---|---|---|---|
| MDA-MB-468 (Breast) | 3.77 nM | 3.42 nM | 1.9 nM |
| NCI-H1299 (Lung) | 60.3 nM | 108 nM | 1.82 nM |
| NCI-H460 (Lung) | 29.5 nM | 171.1 nM | 1.66 nM |
| Capan-2 (Pancreas) | 56.7 nM | 83.6 nM | 7.91 nM |
| MiaPaCa-1 (Pancreas) | 37.3 nM | 38.9 nM | 1.32 nM |
| HT29 (Colorectal) | 92.2 nM | 70.6 nM | 1.07 nM |
| HCT116 (Colorectal) | 7.6 nM | 11 nM | 0.87 nM |
| PC-3 (Prostate) | 34.4 nM | 29.5 nM | 0.9 nM |

Example 10

Flow Cytometry Assays

Methods

Figure 17:
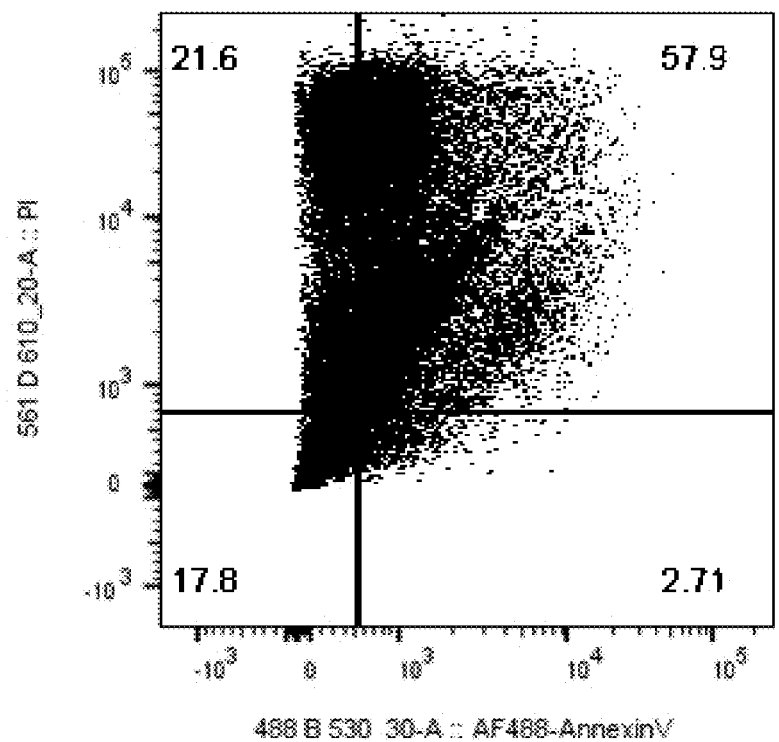
FIG. 17. A representative scatter plot of flow cytometry results for MDA-MB-468 cells treated with 5 μM of CLR1601 for 72 hours. Annexin V (attached to AlexaFluor 488) is shown on the x-axis, while phosphatidylinositide ("PI") is shown on the y-axis. The lower left quadrant indicates live cells, the upper left quadrant indicates necrotic cells, the upper right quadrant indicates late apoptotic cells and the lower right quadrant indicates early apoptotic cells.

Annexin V and PI (phosphatidylinositide) staining by flow cytometry was utilized to determine percentages of live, early apoptotic, late apoptotic, and necrotic cells. In short, cells were treated with cytotoxic agents and stained with an Annexin V/PI labeling kit (Life Technologies). Cells were analyzed on an LSRII flow cytometer (BD Biosciences). As shown in Tables 3-9, cells were classified as: Live (Annexin V negative, PI negative), Early apoptotic (Annexin V positive, PI negative), Late apoptotic (Annexin V positive, PI positive), and Necrotic (Annexin V negative, PI positive). A representative scatter plot is shown in FIG. 17 for MDA-MB-468 cells treated with 5 µM of CLR1601 for 72 hours. Annexin V (attached to AlexaFluor 488) is shown on the x-axis, while PI is shown on the y-axis. The lower left quadrant indicates live cells, the upper left quadrant indicates necrotic cells, the upper right quadrant indicates late apoptotic cells and the lower right quadrant indicates early apoptotic cells. Debris was eliminated from this analysis.

Results

MDA-MB-468 cells, a triple negative breast cancer cell line, were treated with CLR conjugates (CLR1601 and CLR1603) for 72 hours and with paclitaxel ("PTX") for 24 hours. See Table 3. MDA-MB-468 cells, were also treated with CLR conjugates (CLR1606 and CLR1607) for 72 hours and with geldanamycin ("GEL") for 48 hours. See Table 4. For PTX conjugates, cell viability was reduced from 61.1% (no drug treatment) to 17.0%, 17.8%, 22.2%, 19.7%, 53.8%, and 48.9% after treatment with 1 µM CLR1601, 5 µM CLR1601, 1 µM CLR1603, 5 µM CLR1603, 100 nM PTX, and 1 µM PTX, respectively. See Table 3. For GEL conjugates, cell viability was reduced from 61.1% to 58.8%, 42.7%, 52.7%, 56.9%, and 26.2% after treatment with 1 µM CLR1606, 10 µM CLR1606, 1 µM CLR1607, 10 µM CLR1607, and 1 µM GEL, respectively. See Table 4.

TABLE 3

MDA-MB-468 Treated with Paclitaxel Conjugates for 72 Hours

| MDA-MB-468 (% of total cells) | 72 hrs No Drug | CLR1601 (1 uM) | CLR1601 (5 uM) | CLR1603 (1 uM) | CLR1603 (5 uM) | PTX (100 nM) | PTX (1 uM) |
|---|---|---|---|---|---|---|---|
| Live | 61.1 | 17 | 17.8 | 22.2 | 19.7 | 53.8 | 48.9 |
| Necrotic | 2.83 | 15.8 | 21.6 | 22 | 22.5 | 8.89 | 10.8 |
| Late Apoptotic | 20.5 | 57.5 | 57.9 | 49.1 | 55.2 | 31.4 | 34.8 |
| Early Apoptotic | 15.5 | 9.83 | 2.71 | 6.74 | 2.65 | 5.9 | 5.5 |

TABLE 4

MDA-MB-468 Cells Treated with Geldanamycin Conjugates for 72 Hours

| MDA-MB-468 (% of total cells) | 72 hrs No Drug | CLR1606 (1 uM) | CLR1606 (10 uM) | CLR1607 (1 uM) | CLR1607 (10 uM) | GEL (1 uM) |
|---|---|---|---|---|---|---|
| Live | 61.1 | 58.8 | 42.7 | 52.7 | 56.9 | 26.2 |
| Necrotic | 2.83 | 2.31 | 19.4 | 1.62 | 1.63 | 16.3 |
| Late Apoptotic | 20.5 | 25.7 | 33.8 | 25.1 | 26.4 | 37.9 |
| Early Apoptotic | 15.5 | 13.2 | 4.13 | 20.6 | 15.1 | 19.6 |

COLO 829 cells, a melanoma cell line, were treated with GEL conjugates (CLR1606 and CLR1607) for 72 hrs and GEL for 48 hours. See Table 5. Cell viability was reduced from 80.8% (no drug treatment) to 70.4%, 21.1%, 67.9%, 54.3%, 32.4%, and 18.6% after treatment with 1 μM CLR1606, 10 μM CLR1606, 1 μM CLR1607, 10 μM CLR1607, 100 nM GEL, and 1 μM GEL, respectively. See Table 5.

TABLE 5

COLO 829 Cells Treated with Geldanamycin Conjugates for 72 Hours

| COLO 829 (% of total cells) | 72 hrs No Drug | CLR1606 (1 uM) | CLR1606 (10 uM) | CLR1607 (1 uM) | CLR1607 (10 uM) | GEL (100 nM) | GEL (1 uM) |
|---|---|---|---|---|---|---|---|
| Live | 80.8 | 70.4 | 21.1 | 67.9 | 54.3 | 32.4 | 18.6 |
| Necrotic | 1.74 | 1.59 | 28.6 | 2.3.6 | 16.1 | 4.9 | 6.42 |
| Late Apoptotic | 4.18 | 6.7 | 40.1 | 9.05 | 20.9 | 40.8 | 53.7 |
| Early Apoptotic | 13.3 | 21.3 | 10.2 | 20.7 | 8.69 | 21.9 | 21.4 |

PANC-1 cells, a pancreatic cancer cell line, were treated with GEL conjugates (CLR1606 and CLR1607) for 72 hrs and GEL for 48 hours. See Table 6. Cell viability was reduced from 44.2% (no drug treatment) to 42.0%, 21.5%, 44.0%, 33.0%, 23.3%, and 18.9% after treatment with 1 μM CLR1606, 10 μM CLR1606, 1 μM CLR1607, 10 μM CLR1607, 100 nM GEL, and 1 μM GEL, respectively. See Table 6.

TABLE 6

PANC-1 Cells Treated with Geldanamycin Conjugates for 72 Hours

| PANC-1 (% of total cells) | 72 hrs No Drug | CLR1606 (1 uM) | CLR1606 (10 uM) | CLR1607 (1 uM) | CLR1607 (10 uM) | GEL (100 nM) | GEL (1 uM) |
|---|---|---|---|---|---|---|---|
| Live | 44.2 | 42 | 21.5 | 44 | 33 | 23.3 | 18.9 |
| Necrotic | 47.9 | 46.8 | 65.3 | 48.1 | 54.7 | 59.4 | 66.4 |
| Late Apoptotic | 5.65 | 8.63 | 12.6 | 4.83 | 9.81 | 12.6 | 12.8 |
| Early Apoptotic | 2.23 | 2.59 | 0.63 | 3.1 | 2.43 | 4.68 | 1.93 |

22RV1 cells, a prostate cancer cell line, were treated with GEL conjugates (CLR1606 and CLR1607) for 72 hrs and GEL for 48 hours. See Table 7. Cell viability was 20.3%, 21.3%, 16.0%, 21.9%, 15.7%, 19.4%, and 28.1% after treatment with no drug, 1 μM CLR1606, 10 μM CLR1606, 1 μM CLR1607, 10 μM CLR1607, 100 nM GEL, and 1 μM GEL, respectively. See Table 7. Basal cell death was high with this cell line; the cells did not respond well to the method of cell collection.

TABLE 7

22RV1 Cells Treated with Geldanamycin for 72 Hours

| 22RV1 (% of total cells) | 72 hrs No Drug | CLR1606 (1 uM) | CLR1606 (10 uM) | CLR1607 (1 uM) | CLR1607 (10 uM) | GEL (100 nM) | GEL (1 uM) |
|---|---|---|---|---|---|---|---|
| Live | 20.3 | 21.3 | 16 | 21.9 | 15.7 | 19.4 | 28.1 |
| Necrotic | 49.5 | 51.7 | 57.7 | 55.2 | 59.1 | 47.1 | 46.6 |
| Late Apoptotic | 26.2 | 23.4 | 22.9 | 20.7 | 23.1 | 28.4 | 19.1 |
| Early Apoptotic | 4.1 | 3.63 | 3.44 | 2.27 | 2.19 | 5.09 | 6.22 |

CLR conjugates appear to require a longer treatment period with cells to induce cell death. Treatment of MDA-MB-468 cells with 1 μM CLR1601 and 1 μM CLR1603 for 48 hours resulted in a reduction of cell viability from 86.2% (no drug treatment) to 79.4% and 81.4%, respectively. See Table 8. Treatment of COLO 829 cells with 1 μM CLR1606 and 1 μM CLR1607 for 48 hours resulted in a reduction of cell viability from 91.7% (no drug treatment) to 90.1% and 82.7%, respectively. See Table 9.

TABLE 8

MDA-MB-468 Treated with Paclitaxel Conjugates for 48 Hours

| MDA-MB-468 (% of total cells) | 48 hrs No Drug | CLR1601 (1 uM) | CLR1603 (1 uM) | PTX (100 nM) | PTX (1 uM) |
|---|---|---|---|---|---|
| Live | 86.2 | 79.4 | 81.4 | 77.9 | 73.3 |
| Necrotic | 2.87 | 13.1 | 12.4 | 14.1 | 15.6 |
| Late Apoptotic | 8.33 | 6 | 4.78 | 5.54 | 9.18 |
| Early Apoptotic | 2.56 | 1.49 | 1.4 | 2.47 | 1.97 |

TABLE 9

COLO 829 Cells Treated with Geldanamycin Conjugates for 48 Hours

| COLO 829 (% of total cells) | 48 hrs No Drug | CLR1606 (1 uM) | CLR1607 (1 uM) | GEL (100 nM) | GEL (1 uM) |
|---|---|---|---|---|---|
| Live | 91.7 | 90.1 | 82.7 | 36.1 | 24.6 |
| Necrotic | 5.96 | 6.91 | 8.94 | 22.7 | 22.7 |
| Late Apoptotic | 1.67 | 2.2 | 5.54 | 29 | 38.3 |
| Early Apoptotic | 0.72 | 0.79 | 2.77 | 12.2 | 14.4 |

Overall, PLE-paclitaxel and PLE-geldanamycin conjugates were shown to be capable of reducing tumor cell viability including inducing cell death for a variety of tumor types.

What is claimed is:

1. A therapeutic compound of Formula (V),

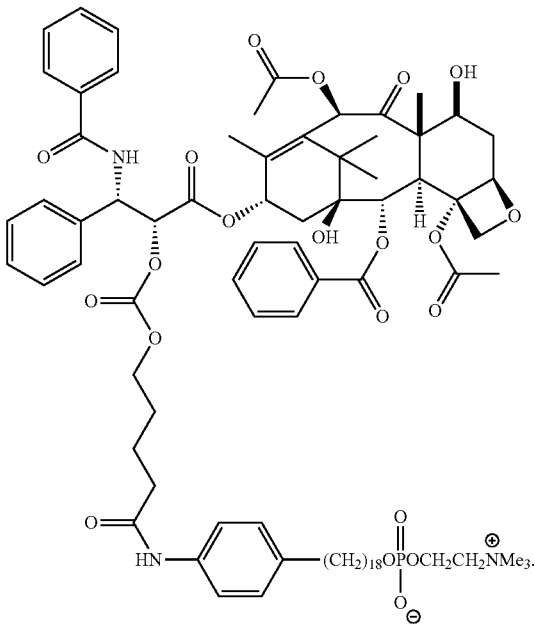

(V)

2. A pharmaceutical composition comprising a therapeutic compound of claim 1 and one or more pharmaceutically acceptable carriers.

* * * * *